(12) United States Patent
Gamache et al.

(10) Patent No.: US 8,851,452 B2
(45) Date of Patent: Oct. 7, 2014

(54) SELF-ALIGNED PLUNGER FOR CHROMATOGRAPHIC VALVE

(75) Inventors: Yves Gamache, Adstock (CA); André Fortier, Adstock (CA)

(73) Assignee: Mecanique Analytique Inc., Thetford-Mines, Quebec (CA)

( * ) Notice: Subject to any disclaimer, the term of this patent is extended or adjusted under 35 U.S.C. 154(b) by 124 days.

(21) Appl. No.: 13/256,381

(22) PCT Filed: Sep. 8, 2009

(86) PCT No.: PCT/CA2009/001250
§ 371 (c)(1),
(2), (4) Date: Sep. 13, 2011

(87) PCT Pub. No.: WO2010/025570
PCT Pub. Date: Mar. 11, 2010

(65) Prior Publication Data
US 2012/0025120 A1   Feb. 2, 2012

Related U.S. Application Data

(60) Provisional application No. 61/165,735, filed on Apr. 1, 2009.

(51) Int. Cl.
| | | |
|---|---|---|
| *F16K 1/00* | (2006.01) | |
| *F16K 15/00* | (2006.01) | |
| *F16K 31/00* | (2006.01) | |
| *G01N 1/00* | (2006.01) | |
| *G01N 30/04* | (2006.01) | |
| *F16K 11/20* | (2006.01) | |
| *F16K 7/16* | (2006.01) | |
| *F16K 51/00* | (2006.01) | |
| *G01N 30/20* | (2006.01) | |

(52) U.S. Cl.
CPC ............ *F16K 7/16* (2013.01); *G01N 2030/205* (2013.01); *G01N 30/20* (2013.01); *F16K 51/00* (2013.01)
USPC .......... 251/335.2; 251/77; 251/334; 251/331; 73/23.41; 73/23.42; 137/597

(58) Field of Classification Search
CPC .... G01N 2030/205; G01N 30/20; F16K 7/16; F16K 11/24; F16K 31/126; F16K 51/00; F16K 7/14
USPC ............. 251/77, 80, 157–204, 333, 334, 337, 251/85, 63.4; 137/468
See application file for complete search history.

(56) References Cited

U.S. PATENT DOCUMENTS 1,710,055 A * 4/1929 Grant .............................. 116/55
1,765,027 A * 6/1930 Mitchell ......................... 429/54
(Continued)

FOREIGN PATENT DOCUMENTS

JP   2004255431   9/2004

OTHER PUBLICATIONS

International Search Report, Dec. 7, 2010.

*Primary Examiner* — John K Fristoe, Jr.
*Assistant Examiner* — Hailey K Do
(74) *Attorney, Agent, or Firm* — Price Heneveld LLP

(57) ABSTRACT

Plungers and plunger assemblies for a diaphragm-sealed valve are provided. Each plunger is adapted to be received in a passage of the valve body and includes a base member and an upper member having a transversal play in this passage with respect to the base member. A resilient middle element is provided between the upper and base member. The base member is connected to a plunger actuating mechanism within the valve body. The upper member may therefore be self-aligning within the passage.

15 Claims, 17 Drawing Sheets

(56) References Cited

U.S. PATENT DOCUMENTS

| | | | |
|---|---|---|---|
| 2,615,465 A * | 10/1952 | Woodward | 137/243.2 |
| 3,111,849 A | 11/1963 | Broerman | |
| 3,140,615 A | 7/1964 | Broerman | |
| 3,198,018 A | 8/1965 | Broerman | |
| 3,376,894 A | 4/1968 | Broerman | |
| 3,387,496 A | 6/1968 | Broerman | |
| 3,417,605 A | 12/1968 | Hahn | |
| 3,439,542 A | 4/1969 | McCray | |
| 3,492,873 A | 2/1970 | Broerman et al. | |
| 3,545,491 A | 12/1970 | Broerman | |
| 3,613,729 A * | 10/1971 | Dora | 137/614.18 |
| 3,633,426 A | 1/1972 | Broerman | |
| 3,671,009 A | 6/1972 | Stampfli | |
| 4,112,766 A | 9/1978 | Ragains | |
| 4,276,907 A | 7/1981 | Broerman | |
| 4,333,500 A | 6/1982 | Broerman | |
| 4,372,333 A * | 2/1983 | Goans | 137/1 |
| 4,474,889 A * | 10/1984 | Terry et al. | 436/161 |
| 4,682,757 A | 7/1987 | Shelton | |
| 5,601,115 A | 2/1997 | Broerman | |
| 6,202,698 B1 | 3/2001 | Stearns | |
| 6,896,239 B1 | 5/2005 | Brenes | |
| 7,216,528 B2 | 5/2007 | Gamache et al. | |
| 7,537,194 B2 | 5/2009 | Nagai | |
| 7,931,043 B2 | 4/2011 | Gamache et al. | |

* cited by examiner

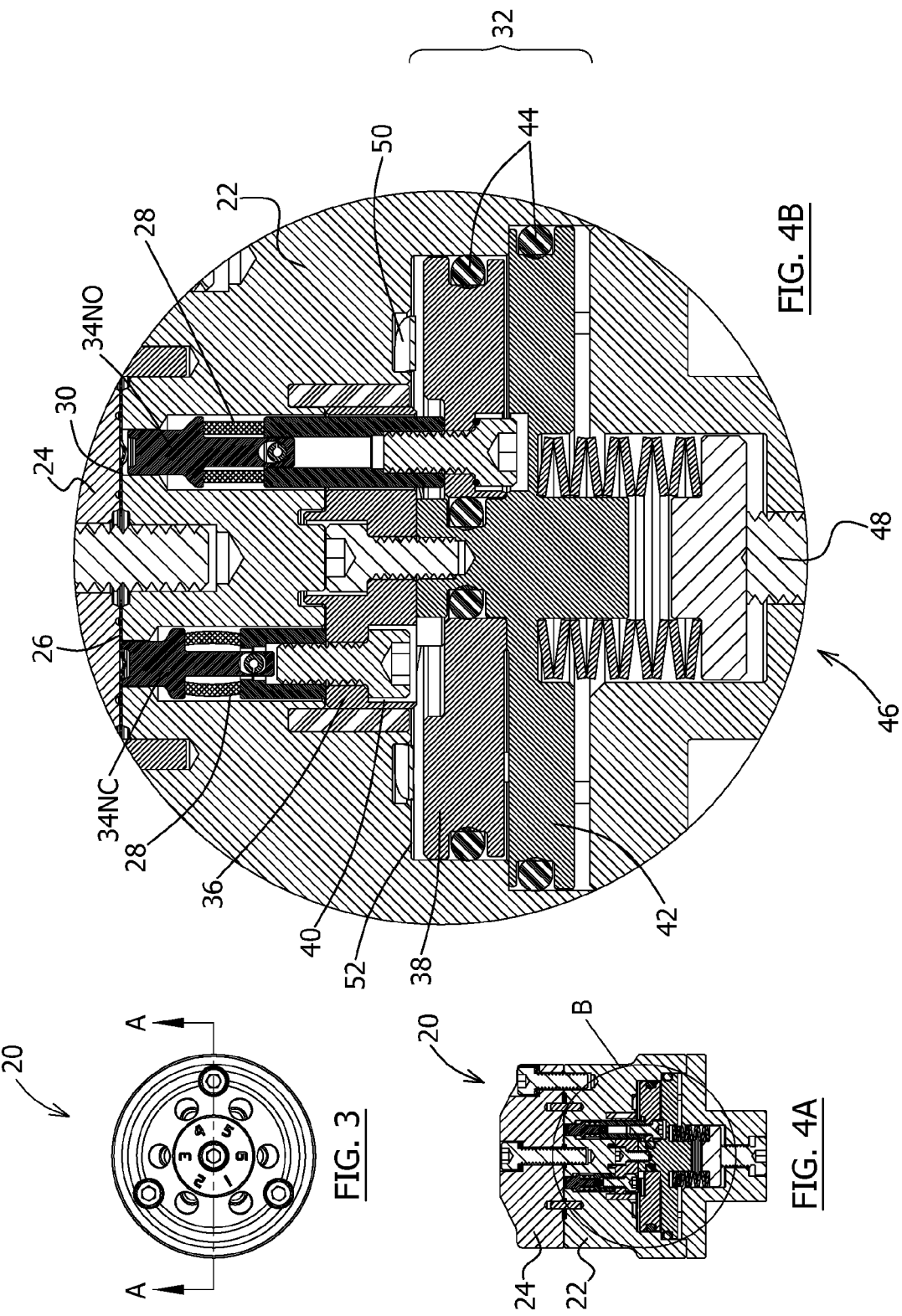

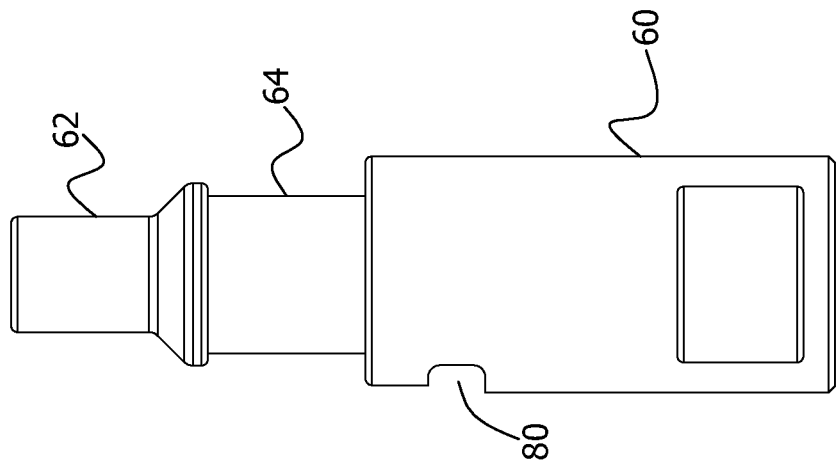
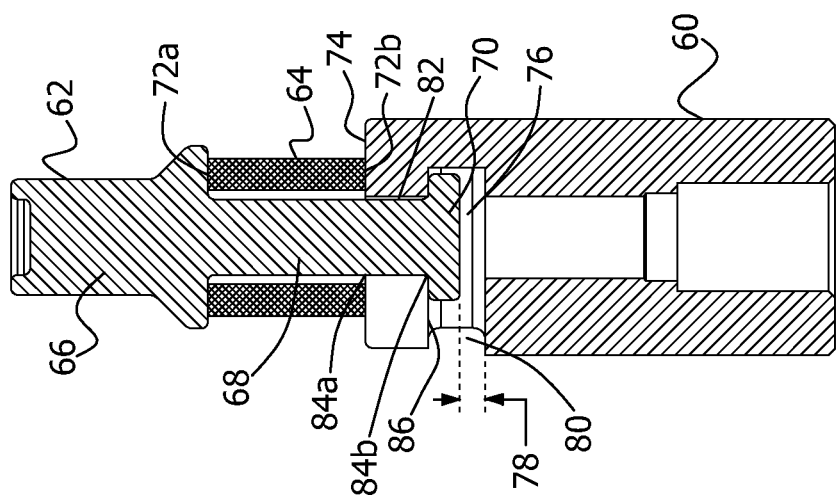
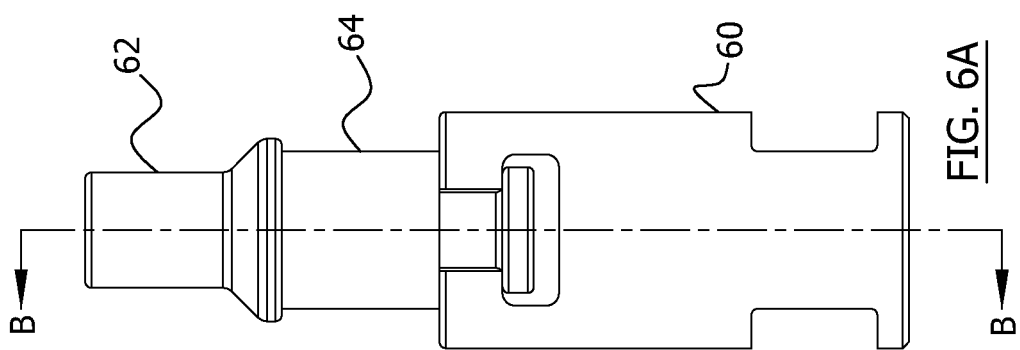
FIG. 6C
FIG. 6B
FIG. 6A

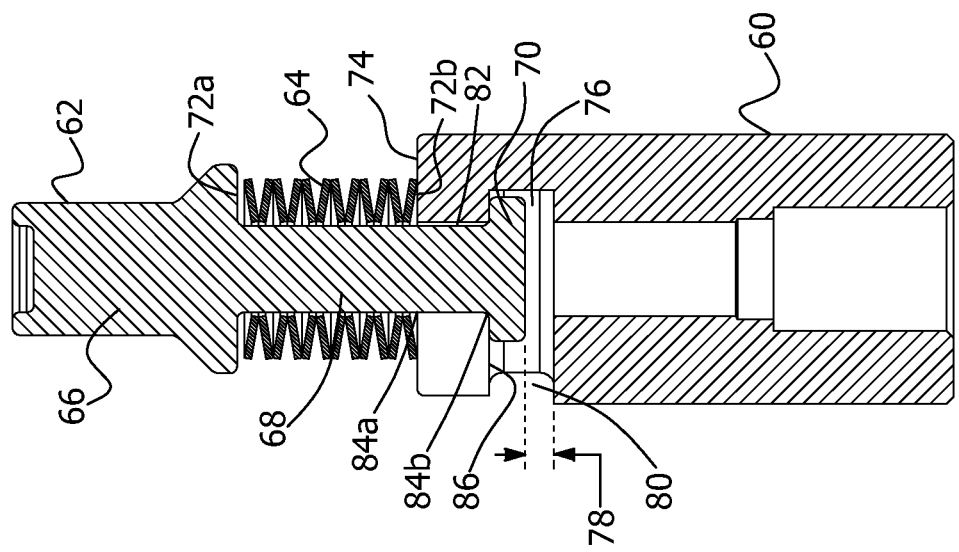
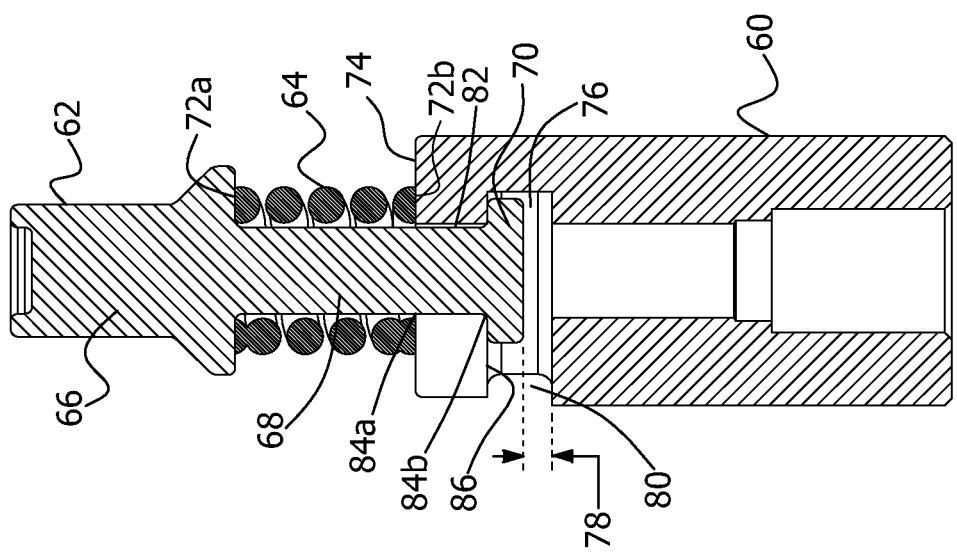

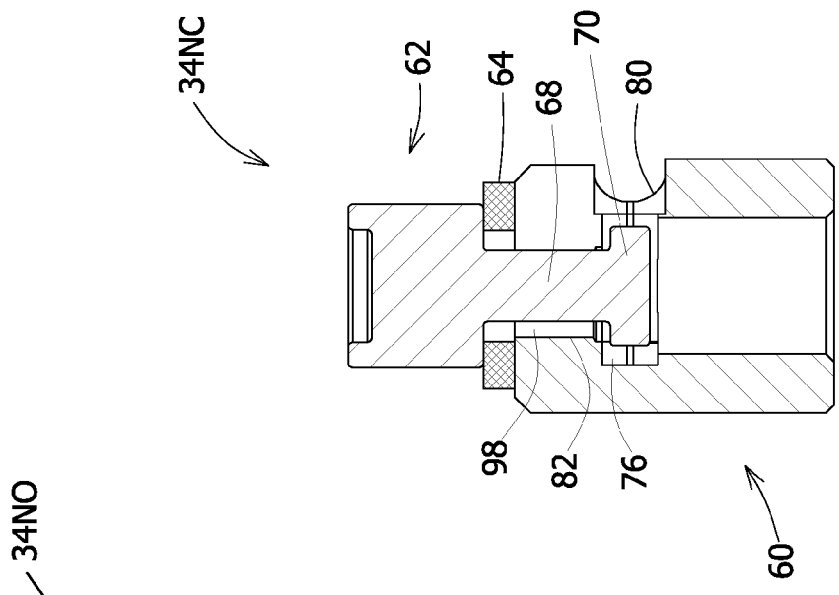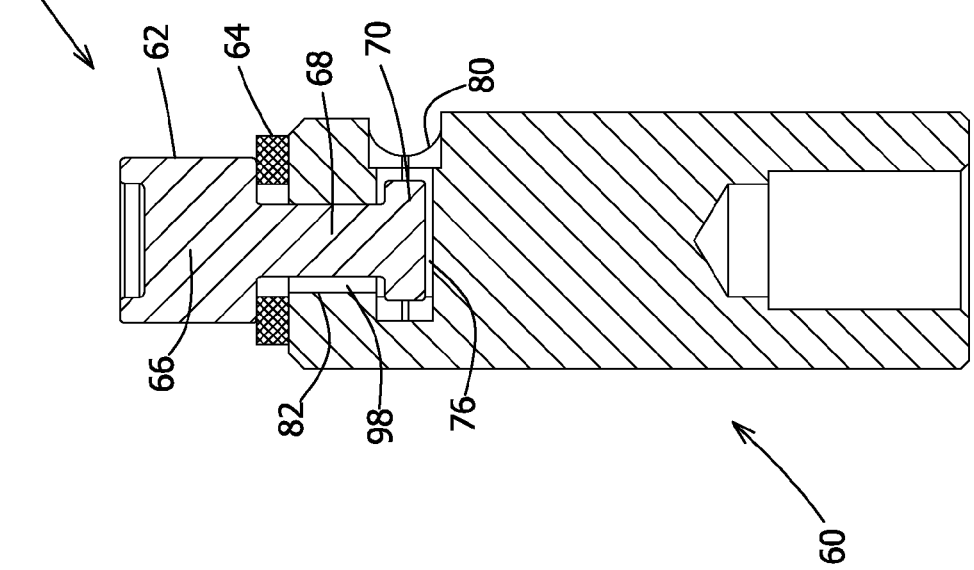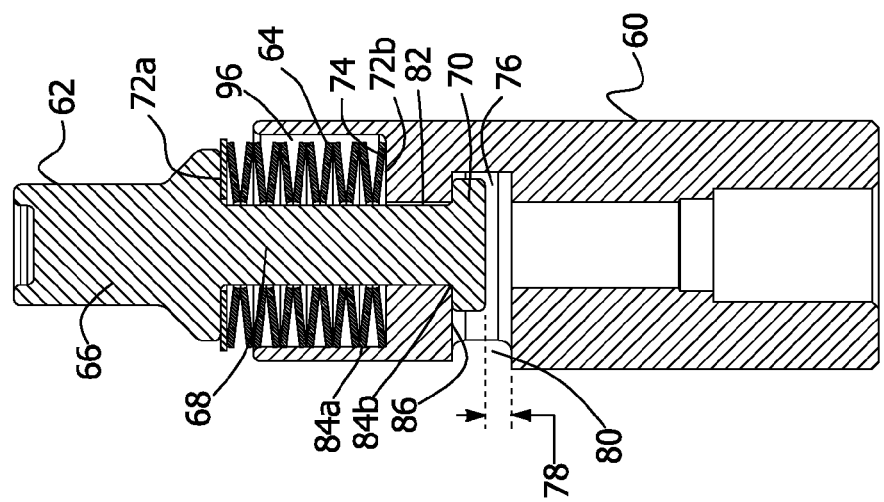

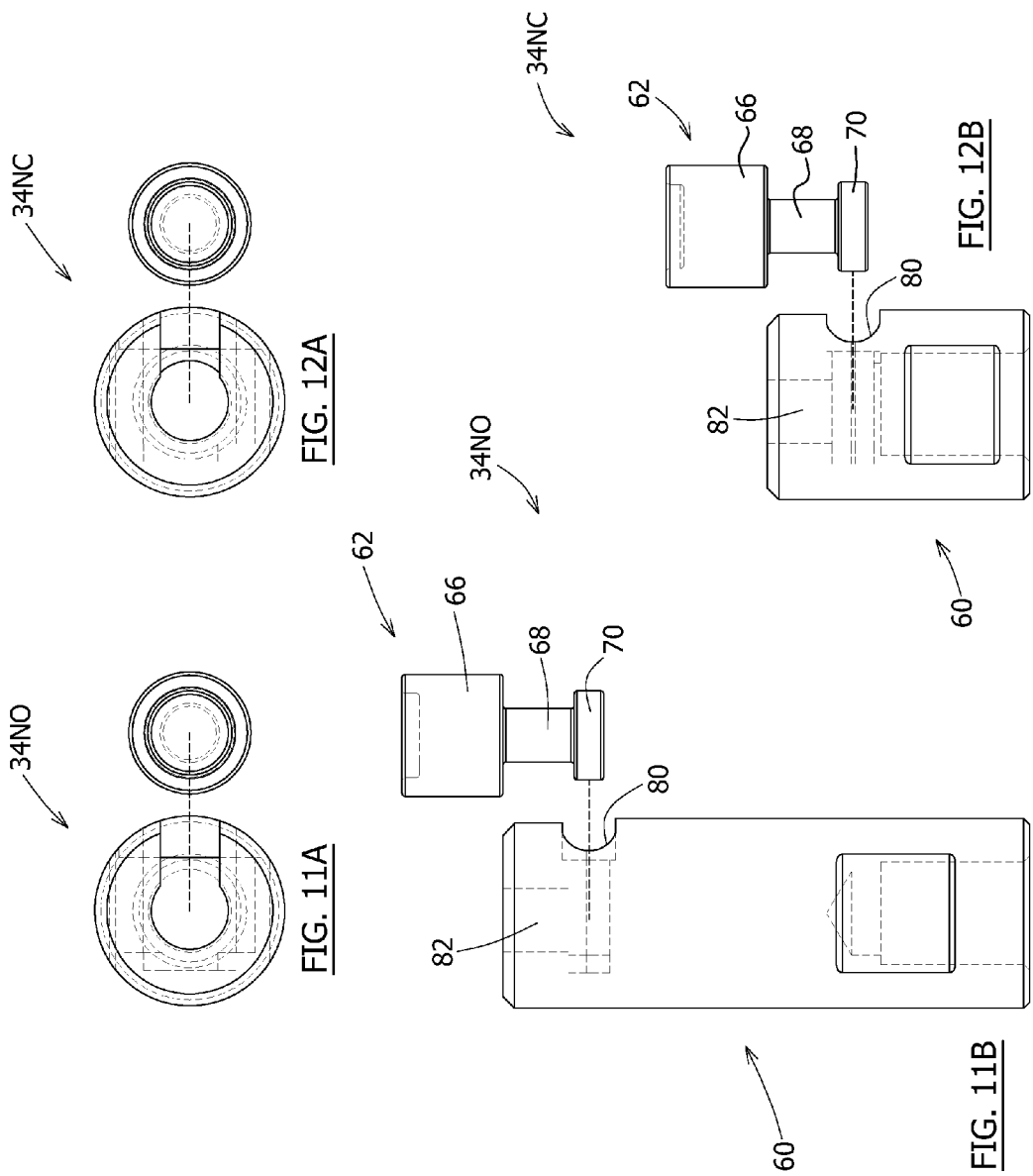

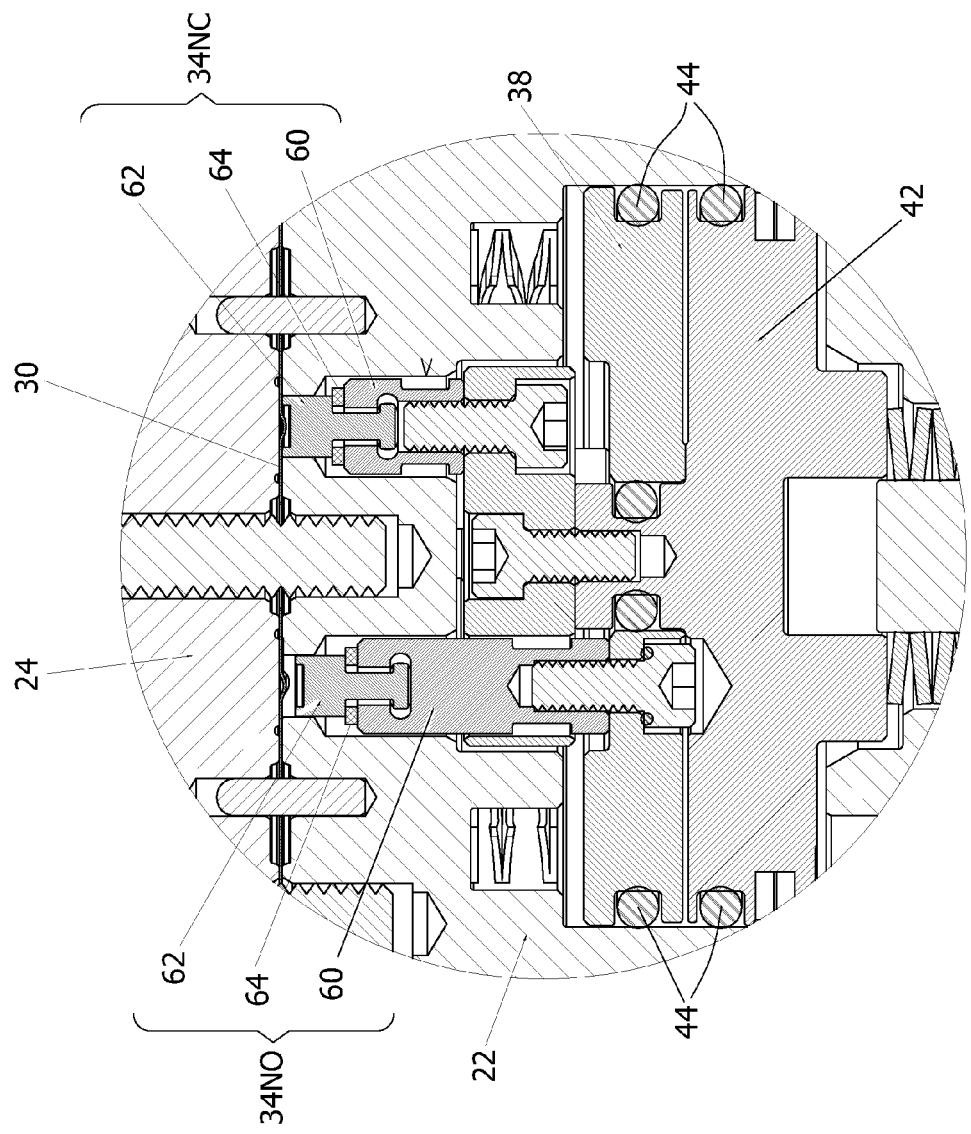
DETAIL A
FIG. 13C
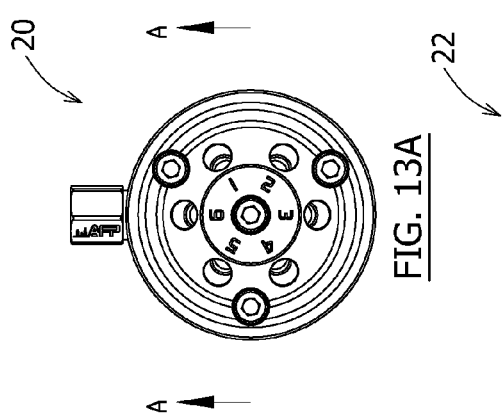
FIG. 13A
SECTION A-A
FIG. 13B

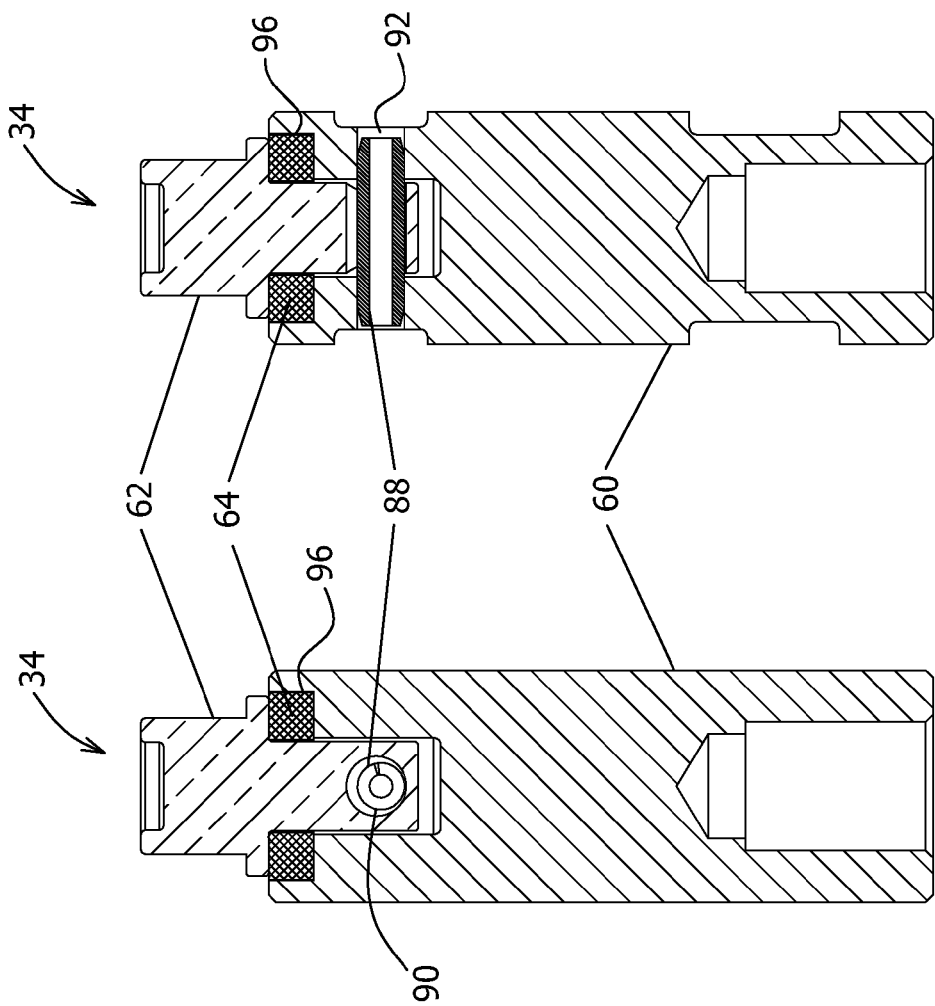
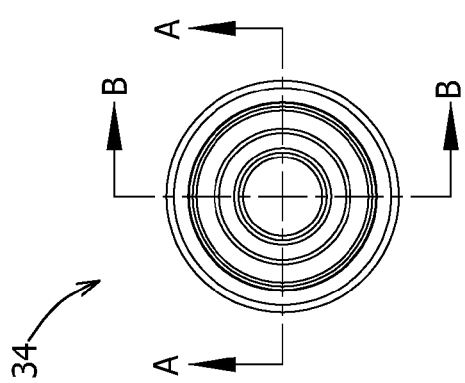
FIG. 14

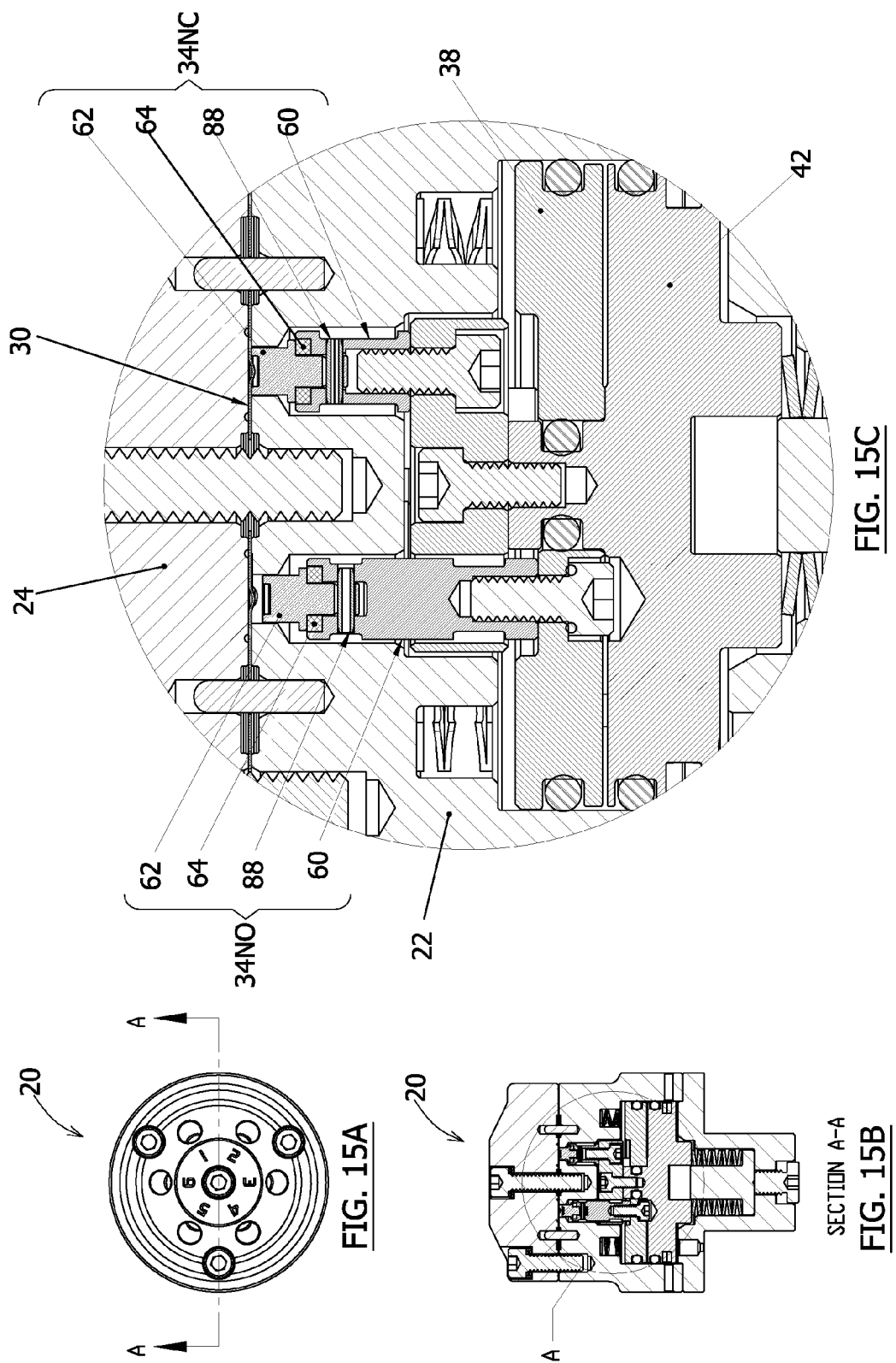

SELF-ALIGNED PLUNGER FOR CHROMATOGRAPHIC VALVE

CROSS REFERENCE TO RELATED APPLICATIONS

This application claims the benefit of U.S. Provisional Patent Application No. 61/165,735, filed on Apr. 1, 2009, entitled "SELF-ALIGNED PLUNGER FOR CHROMATOGRAPHIC VALVE," the entire disclosure of which is incorporated herein by reference.

FIELD OF THE INVENTION

The present invention generally relates to gas chromatography and more particularly concerns a valve therefor adapted to a wide range of temperatures.

BACKGROUND

Chromatographic systems rely on the use of valves to allow reproducible sample introduction and various column switching schemes. Diaphragm-sealed type valves are commonly used in such systems. A typical diaphragm-sealed valve includes a valve cap having a plurality of ports opening on an interface. Each port is linked to a passage in the valve cap to which various analytical fitting and tubing may be connected. A diaphragm valve also includes a valve body having an interface opposite that of the valve cap. The diaphragm, generally made of a polymer material, is compressibly positioned between the opposite interfaces of the valve body and valve cap. A main recess is usually provided in the interface of the valve body, in which sits a matching recess in the diaphragm, allowing some clearance for fluid circulation between adjacent ports. This communication between ports can be stopped through the use of plungers slideably mounted in the valve body. Each plunger can press on the diaphragm between two adjacent ports, and therefore prevent fluid communication therebetween.

Examples of diaphragm-sealed valve can for example be seen in U.S. Pat. Nos. 3,111,849; 3,140,615; 3,198,018; 3,376,894; 3,387,496; 3,417,605; 3,439,542; 3,492,873; 3,545,491; 3,633,426; 4,112,766; 4,276,907; 4,333,500; 5,601,115; 6,202,698 and 7,216,528.

One of the problems of prior art diaphragm valves for gas chromatography is that the valve performance can vary greatly as a function of the operating temperature to which it is submitted. Variations in leak rate can be observed at moderate pressure, for example when the operating temperature is cycles such as is the case in temperature programming mode, or simply when the valve is operate continuously at temperature up to 350° or 400° C.

This performance variation is related to the fact that material dimensions of all the valve components, as well as the elasticity or the hardness of the polymer diaphragm, change with the temperature.

On the one hand, requirements for diaphragm-sealed valve design suitable for gas chromatography applications involve tight manufacturing tolerances for flatness, parallelism, in the surface finishes, and length of various components, especially the valve's plungers. Variations in plunger length will have a dramatic impact in the valve performance. The total effect of temperature induced dimension changes will generate leaks, particularly if the valve is subjected to rapid and large temperature variations that may generate distortions and continuous dimensions variation.

On the other hand, diaphragm variations in extreme conditions may be crucial as they can lead to permanent damage of the valve. In the prior art, the actuating pressure on the plungers, and the resulting force applied when a plunger is pushed against this diaphragm to interrupt fluid flow between two ports, does not vary with temperature. However, at high operating temperatures, the polymer diaphragm becomes softer and this same force may lead to permanent damage, by pushing away the material underneath the plunger area or simply by punching or leaving permanent marking on the diaphragm.

Referring to FIGS. 1, 1A and 1B (PRIOR ART), there is shown a typical pneumatic operating mechanism for the plungers of a diaphragm-sealed valve. Such a mechanism includes two sets of plungers, respectively designated as "normally closed and "normally opened" plungers, each set being attached to a corresponding piston. When a piston is moved into an upper position, it forces the corresponding plungers up against the diaphragm. Normally, the actuating pneumatic pressure of each piston is set to a value sufficient to generate the required force on the corresponding plungers to seal the diaphragm between ports, without over stressing the diaphragm.

Diaphragm-sealed valves are normally operated with the help of a three way electric solenoid valve. When the solenoid valve is powered ON (see FIG. 2 (PRIOR ART)), the actuating pressure is applied into actuating mechanism and when the solenoid valve is powered OFF (such as shown in FIG. 1B (PRIOR ART)), the pressure is evacuated from the actuator, normally to the atmosphere.

The stroke of the pistons is limited by the plungers pressing against the valve diaphragm. As a result, increasing the actuating pressure increases the force applied on the diaphragm by the plungers. Typical actuating pressure values for diaphragm-sealed valves range from 50 to 65 PSIG. If the available actuating pressure from the solenoid valve is higher, as is normally the case in a process plant environment where 125 PSIG are usually available, a pressure regulator must be use to decrease the supplied pressure to a safe level. This requires another piece of hardware and associated tubing inside the instrument, increasing the overall cost and necessitating a larger equipment inventory.

When a valve as shown in FIG. 1 is actuated at a typical actuating pressure, for example 60 PSIG, and the temperature is ramped up, another problem may appear, depending on the system configuration. The pressurized volume inside the valve is ramped up from ambient temperature to 300° C., generating a pressure rise of about 60 PSIG. This results in a final pressure inside the system of roughly about 120 PSIG. This generates an uncontrolled extra force on the diaphragm that contributes to diminished valve performance over the time. Since the resulting increase in force acting on the diaphragm coincides with operating conditions where the diaphragm material is softened by the high temperature, operating under these conditions will reduce dramatically the valve performance and lifetime.

In addition, it is known that slight variations in the manufacturing process or assembly may cause a plunger to be slanted or misaligned within the plunger, which can negatively effect the valve's operation.

There is therefore a need for a diaphragm-sealed type valve which alleviates at least some of the drawbacks of the prior art.

SUMMARY OF THE INVENTION

In accordance with one aspect of the invention, there is provided a plunger for a diaphragm-sealed valve, the valve having a valve body provided with at least one passage extending in the valve body and opening on a diaphragm-contacting surface, a plunger-actuating mechanism being located within the valve body, said plunger being sized to slidably fit in a corresponding one of the at least one passage of the valve body and comprising:
- a base member operatively connectable to the actuating mechanism;
- an upper member projecting towards said diaphragm-contacting surface when in said passage, said upper member having a transversal play within said passage with respect to the base member; and
- a resilient middle element provided between the base member and the upper member.

Advantageously, misalignments of the plunger relative to its corresponding passage may be compensated for by allowing the upper member of the plunger to align itself with the passage, thereby improving the overall valve performances.

In accordance with another aspect of the invention, there is further provided a plunger assembly for a diaphragm-sealed valve, the valve having a valve body provided with a plurality of passages extending in the valve body and opening on a diaphragm-contacting surface, said plunger assembly comprising:
- a plunger-actuating mechanism located within the valve body; and
- a plurality of plungers each slidably provided in a corresponding one of the passage of the valve body, each plunger comprising:
  - a base member operatively connected to the actuating mechanism;
  - an upper member projecting towards said diaphragm-contacting surface when in said passage, said upper member having a transversal play within said passage with respect to the base member; and
  - a resilient middle element provided between the base member and the upper member.

In one embodiment, an adjustable attachment connects the base member of each plunger to the plunger-actuating mechanism, therefore allowing a fine-tuning of the distance therebetween.

Other features and advantages of the present invention will be better understood upon reading of preferred embodiments thereof with reference to the appended drawings.

BRIEF DESCRIPTION OF THE DRAWINGS

FIG. 3 is a top view of a diaphragm-sealed valve provided with plungers according to embodiments of the invention.

FIG. 4A is a cross sectional view along lines A-A the valve of FIG. 3, and FIG. 4B is an enlargement of a portion of FIG. 4A, showing a portion of a plunger assembly according to an embodiment of the present invention before actuation.

FIG. 6A is a side view of a plunger according to an embodiment of the invention; FIG. 6B is a cross-sectional view along lines B-B of FIG. 6A; FIG. 6C is a side view of the plunger of FIG. 6A from a perpendicular direction.

FIGS. 7A and 7B are cross-sectional views of plungers according to variants of the embodiment of FIGS. 6A to 6C, provided with different types of resilient middle elements.

FIG. 9 is a cross-sectional view of a plunger according to another embodiment of the invention, wherein a portion of the resilient middle element is received within a recess in the base member.

FIGS. 10A and 10B are cross-sectional views of a plunger according to another embodiment of the invention, wherein the head member of the plunger is self-aligning.

FIG. 11A is a top view of the normally open plunger according to an embodiment of the invention, where the upper member is removed from the base member; FIG. 11B is a side view of the plunger of FIG. 11A.

FIG. 12A is a top view of the normally closed plunger according to an embodiment of the invention, where the upper member is removed from the base member; FIG. 12B is a side view of the plunger of FIG. 12A.

FIG. 13A is a top view of a valve according to another embodiment of the invention; FIG. 13B is a cross-sectional view taken along lines A-A of FIG. 13A; FIG. 13C is an enlarged portion A of FIG. 13B showing the plungers of FIGS. 10A and 10B inside the valve.

FIG. 14 is a top view of a plunger according to another embodiment of the invention incorporating a self-aligning head member; FIG. 14A is a cross-sectional view taken along lines A-A of FIG. 14; FIG. 14B is a cross-sectional view taken along lines B-B of FIG. 14.

FIG. 15A is a top view of a valve according to another embodiment of the invention; FIG. 15B is a cross-sectional view taken along lines A-A of FIG. 15A; FIG. 15C is an enlarged portion A of FIG. 15B showing the plungers of FIGS. 10A to 11C inside the valve.

DESCRIPTION OF PREFERRED EMBODIMENTS

Figure 1B:
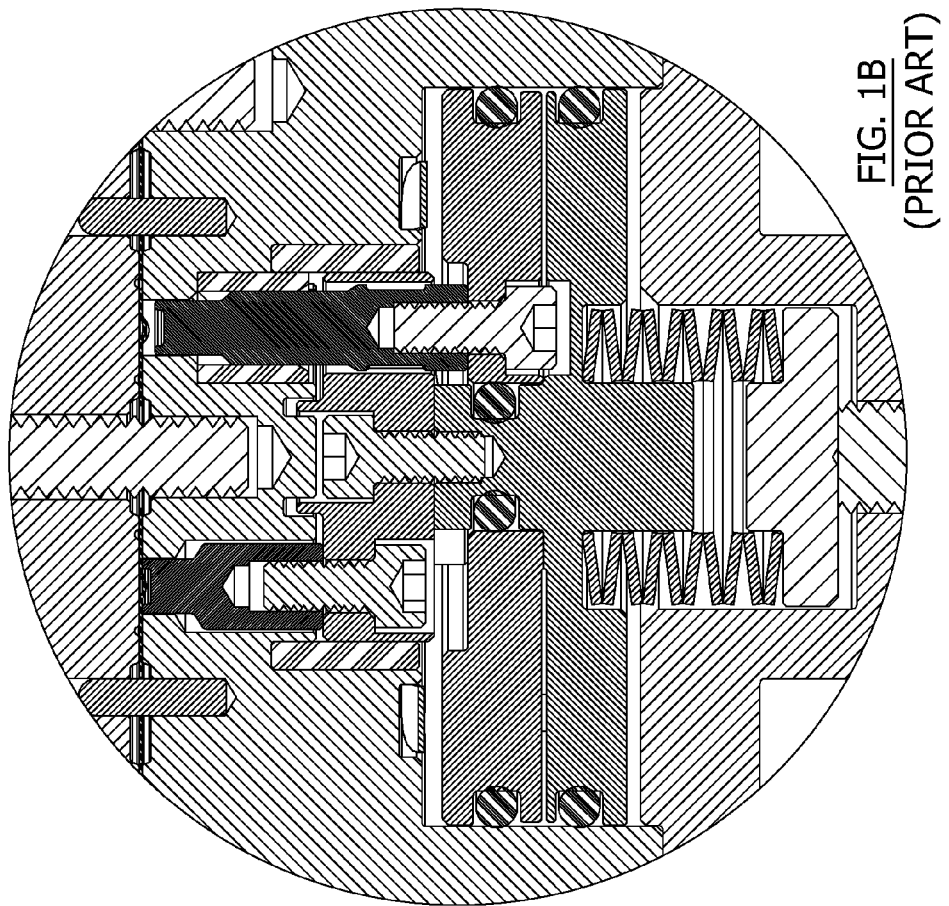
FIG. 1B is an enlargement of portion B of FIG. 1A, and is shown with the actuating mechanism turned "OFF".
Figure 1:
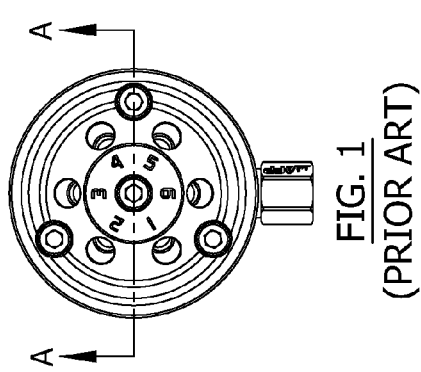
FIG. 1 (PRIOR ART) is a top view of a valve according to prior art.
Figure 1A:
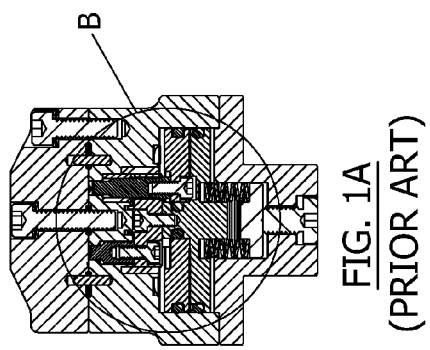
FIG. 1A is a cross-sectional view along lines A-A of FIG. 1.
Figure 2:
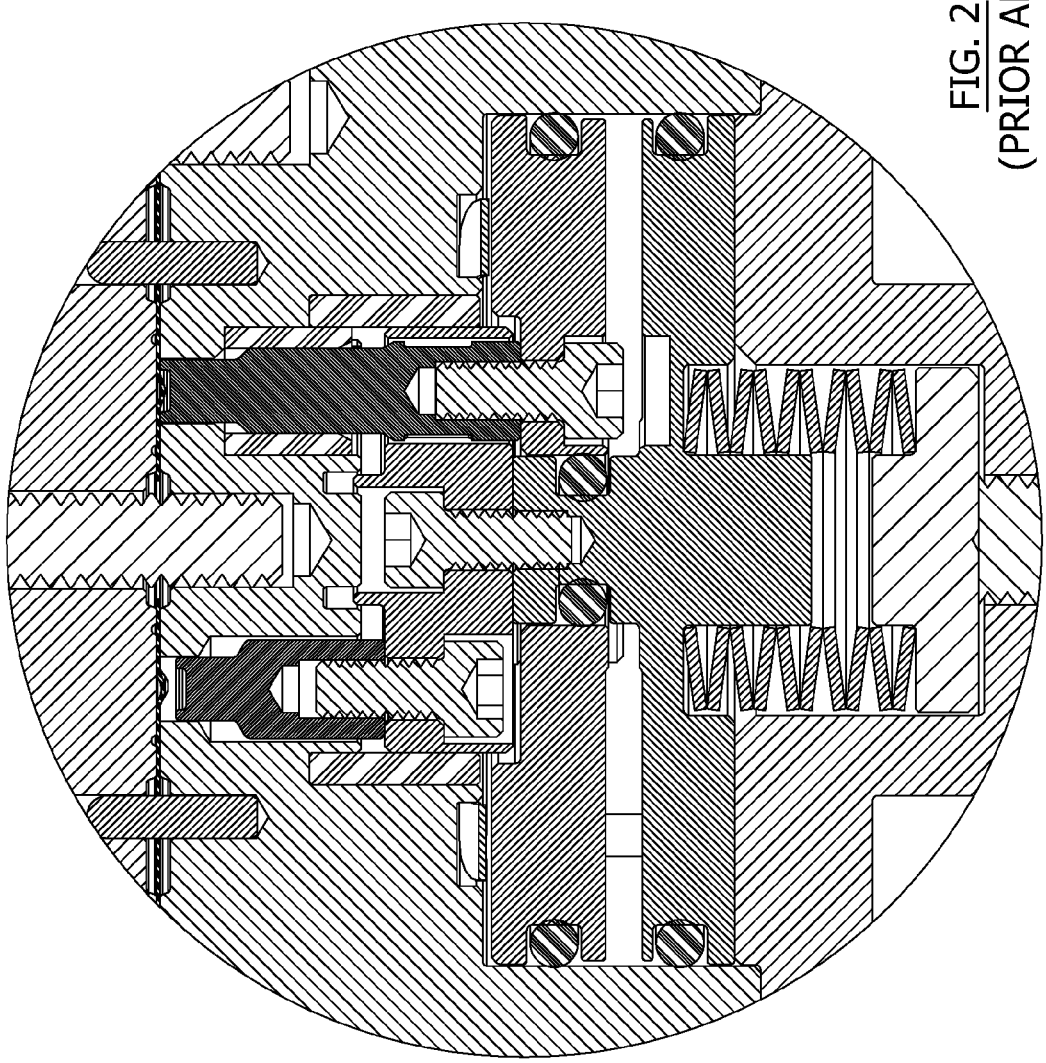
FIG. 2 (PRIOR ART) shows an enlargement of a cross-sectional view of the valve of FIG. 1, shown with the actuating mechanism turned "ON".

The present invention generally relates to plungers and plunger assemblies for diaphragm-sealed valves, for example of type suitable for gas chromatography.

With reference to FIGS. 3, 4A, 4B, 5A and 5B there is shown an example of a portion of an improved plunger assembly for a diaphragm-sealed valve 20, according to an embodiment of the invention. The valve 20 generally includes a valve body 22, a valve cap 24 and a diaphragm compressibly disposed therebetween. For more detail on the construction of a valve of this type, reference can for example be made to international patent application published under no. WO/2009/073966. One or more passage 28 extends in the valve body 22 and open on a diaphragm-contacting surface 30. A plunger-actuating mechanism 32 is located within the valve body.

Figures 5A, 5B:
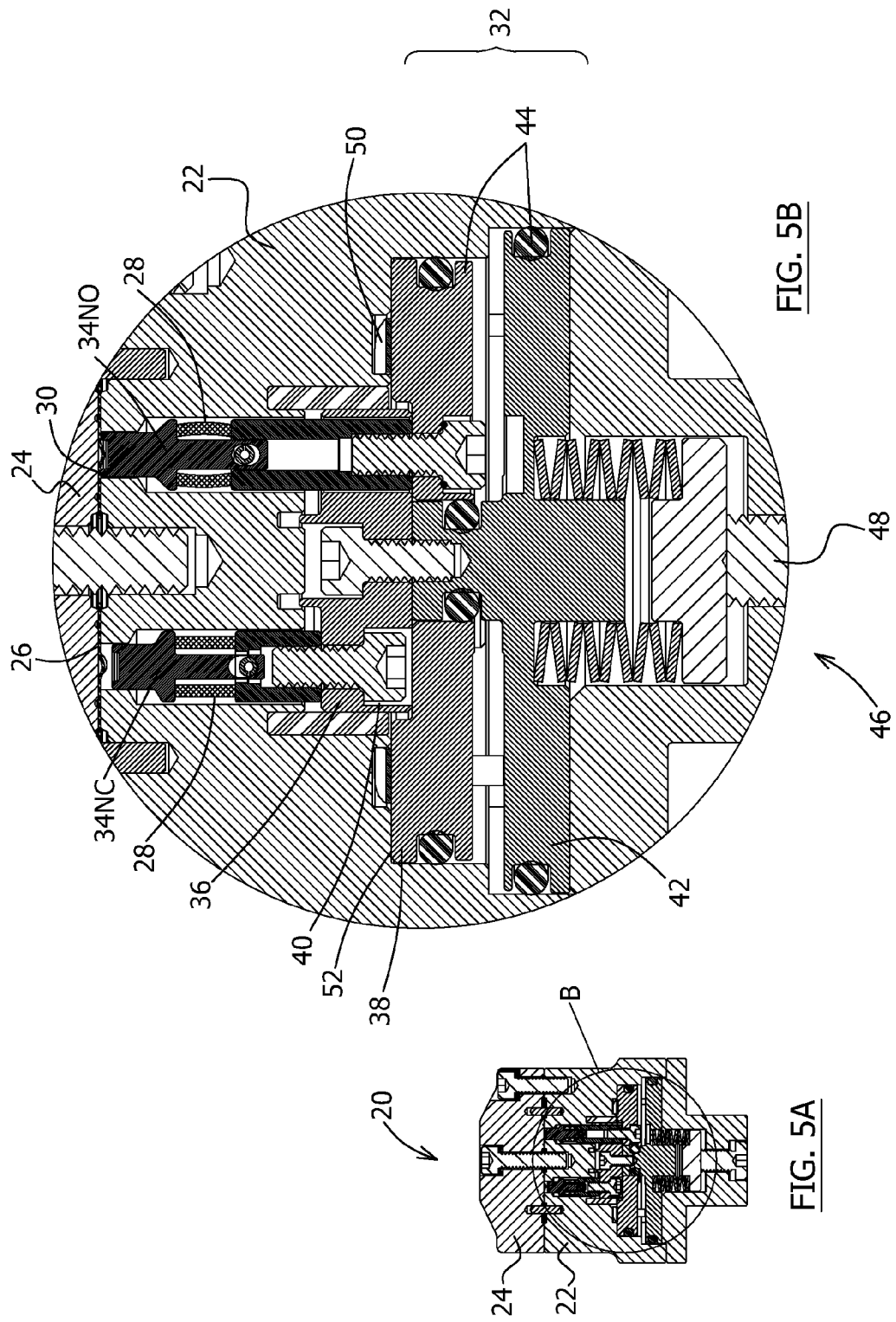
FIG. 5A is a cross sectional view along lines A-A the valve of FIG. 3.
FIG. 5B is an enlargement of a portion of FIG. 5A, showing a portion of a plunger assembly according to an embodiment of the present invention after actuation.

The illustrated embodiment shows a six (6) plungers valve, two (2) of which being shown in FIGS. 4B and 5B. Of course, the present invention may be applied to diaphragm-sealed valves having a different number of plungers. The term "plunger" is understood to mean a mechanical component driven by or against a mechanical force or fluid pressure. The particular construction of plungers 34 according to embodiments of the present invention will be explained further below.

Each plunger 34 is slideable in a corresponding passage 28 of the valve body 22. Preferably, the diameter of a passage 28 is slightly larger than that of its corresponding plunger 34. A guide sleeve (not shown) may surround the passage 28, for facilitating the movement of the plunger 34 into the passage 28. Preferably, when in the closed position, the contact area of each plunger 34 is pushed evenly throughout its surface. Thus, all mechanic or fluid forces are transferred equally onto the diaphragm 26. This design ensures that the plungers 34 remain substantially vertical when actuated.

According to embodiments of the invention, the plungers 34 are preferably of two types, designated as "normally closed" (NC) and "normally open" (NO). In typical chromatography applications, the plungers 34 of a given type are actuated together, so that they are either all in the closed position or all in the open position. As their names indicate, the normally closed plungers 34NC are biased towards the closed position, whereas the normally opened plungers 34NO are biased towards the open position.

In the illustrated embodiment, it can be seen that the normally closed plungers 34NC have a length different than the length of the normally open plungers 34NO. The plunger-actuating mechanism 32 preferably includes a push plate 36 which extends within the valve body 22 in parallel to its diaphragm-contacting surface 30, and is movable transversally thereto. The normally closed plungers 34NC are mounted on the push plate 36. The plunger-actuating mechanism 32 further includes an upper piston 38 extending contiguously under the push plate 36. The normally open plungers 34NO are mounted on the upper piston 38. A plurality of cavities 40 extend across the push plate 36 for allowing the normally open plungers therethrough.

The plunger-actuating mechanism 32 further includes a lower piston 42 extending contiguously under the upper piston 38 and rigidly connected to the push plate 36. The lower piston 42 and push plate 36 therefore move together within the valve body 22. Dowel pins (not shown) may be provided to prevent the upper and lower pistons 38 and 42 from rotating with respect to each other and with respect to the valve body 22, and O-rings 44 are preferably provided to properly seal the upper and lower pistons 38 and 42.

In the illustrated embodiment, a Belleville assembly 46, including a Belleville washer stack and a plate, cooperates with the lower piston 42. The force on the Belleville assembly 46 is preferably controlled by a compression set screw 48. A bottom cap (not shown) may close the valve body 22 at its bottom end. Of course, the Belleville assembly 46 may be replaced by any other biasing means, such as standard springs or polymer bushings.

The upper piston 38 is biased downward by appropriate means. In the illustrated embodiment, disc spring 50 extend from within the valve body 22 over the upper piston 38, and applies a downward force thereon when no opposite force is in play. The normally open plungers 34NO mounted on the upper piston 38 are therefore biased towards the open position. In the upward direction, the stroke of the upper piston 38 is limited by a shoulder 52 machined in the valve body 22.

The actuating mechanism 32 is operable for actuating the plungers 34 of both types between their open and closed positions thereof. This can be accomplished in the current embodiment by controlling the distance between the upper and lower pistons 38 and 42. When not actuated, as shown in FIG. 4B, the two pistons 38 and 42 are in contact, as they are pushed towards each other by the Belleville assembly 46 and disc spring 50. The actuating mechanism 32 preferably includes a pneumatic actuator formed by the two pistons 38 and 42, the push plate 36 and the Belleville assembly 46, and further includes a solenoid valve or other appropriate system for supplying pressurised gas between the upper and lower pistons 38 and 42 through a cylinder port. When the valve is actuated (see FIG. 5B), the gas will counterbalance the bias of both pistons 38 and 42 by pushing the upper piston 38 upward, thus sliding the normally open plungers 34NO towards the closed position, and then pushing the lower piston 42 downwards, thus pulling the push plate 36 downward and retracting the normally closed plungers 34NC towards the open position. Removing the pressurized gas will have the opposite result, due to the biasing effect of the Belleville assembly 46 and disc spring 50.

Referring to FIGS. 6A to 6C, there is shown a first embodiment of a plunger 34 according to an embodiment of the present invention. Each plunger is made of three (3) separate sections: a base member 60, an upper member 62, and a resilient middle element 64. The base member 60 is operatively connected to the plunger-actuating mechanism for collaboration therewith. Preferably, the plungers 34 are affixed to either the push plate or the upper piston through fixed fasteners such as screws, which advantageously allows the valve to be fully operational regardless of its orientation. It will therefore be understood by one skilled in the art that the reference to the directions "up" and "down" or "upper" and "lower" throughout the present application is used for ease of reference to the drawings, and is not meant to indicate a preferred orientation of the valve in use.

The upper member 62 projects towards the diaphragm-contacting surface of the valve body, and will therefore compress the diaphragm when the plunger is in the closed position. In some embodiments, the upper member 62 is interlocked with the base member 60. By "interlocked", it is understood that the upper member 62 and base member 60 are connected directly or indirectly in such a fashion that they are part of a same mechanism. The upper member 62 has a longitudinal play within the passage of the valve body with respect to the base member 60, that is, it is free to move vertically up and down over an appropriate distance with respect to the base member 60.

The resilient middle element 64 is disposed between the base member 60 and upper member 62. When the plunger is at rest, the resilient middle element 64 preferably biases the upper member 62 away from the base member 60. When the pistons are force downwardly, the base member pulls down the upper member to clear the diaphragm.

Referring to FIGS. 6B, 7A and 7B, the upper member 62 of the plunger preferably includes a head portion 66 which projects towards the diaphragm-contacting surface, a neck portion 68 which holds the resilient middle element 64 and an anchor portion 70 interlocked with the base member 60. The resilient middle element 64 is preferably ring shaped, surrounds the neck portion 68 and its opposite ends 72a and 72b respectively abuts on the under face of the head portion 66 and a surface of the base member defining an abutment surface 74. In the embodiments of FIGS. 6B, 7A and 7B, the abutment surface of the base member extends on the top thereof.

Preferably, the anchor portion 70 of the upper member 62 has a width greater than its neck portion 68, and may for example be shaped as a disk as shown in the drawings in reference. The anchor portion 70 is preferably received in a cavity 76 provided in the base member 60, this cavity 76 being sized to provide a longitudinal clearance 78 for the anchor portion 70. In this manner, the upper member can move over a certain range along the longitudinal axis of the plunger 34, thereby defining a longitudinal play between the upper and base member 62 and 60.

Preferably, the upper member 62 and base member 60 are machined to define mating shapes as shown in the drawings. The base member 60 further preferably includes a bore 82 extending longitudinally therein and having opposite extremities 84a and 84b opening on the abutment surface 74 of the base member 60 and on the cavity 76, respectively. The bore 82 is sized to receive therein a section of the neck portion 68 of the upper member 62. The transition between the bore 82 and the cavity 76 defines a shoulder 86 for holding the anchor portion 70 within the cavity 76. The base member 60 preferably has a slot 80 opening on a side thereof providing access to the cavity 76 for assembling the components of the plunger together.

Figure 8A:
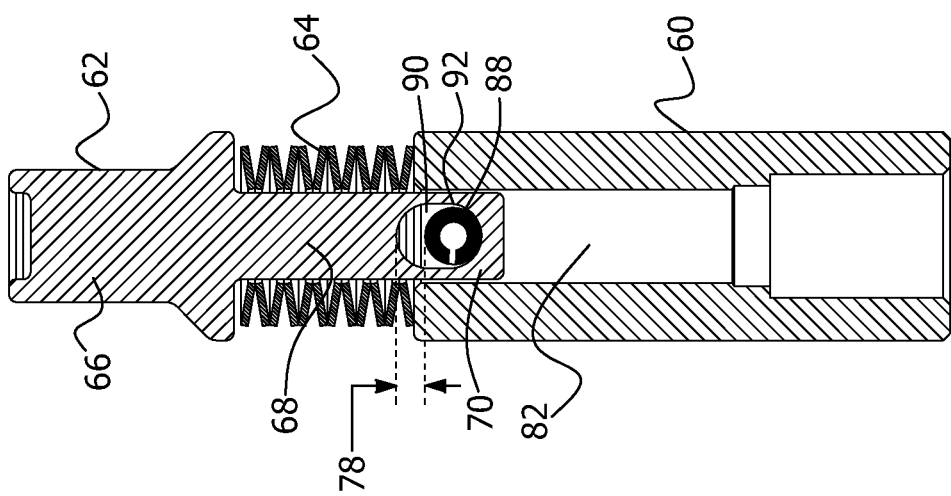
FIG. 8A to 8C are cross-section views of plungers according to a different embodiment of the invention, shown with different types of resilient elements.
Figure 8B:
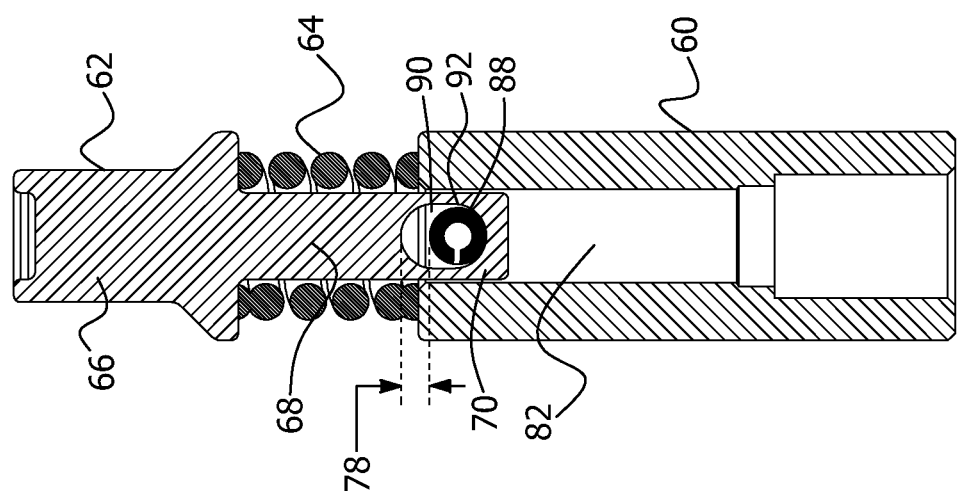
Figure 8C:
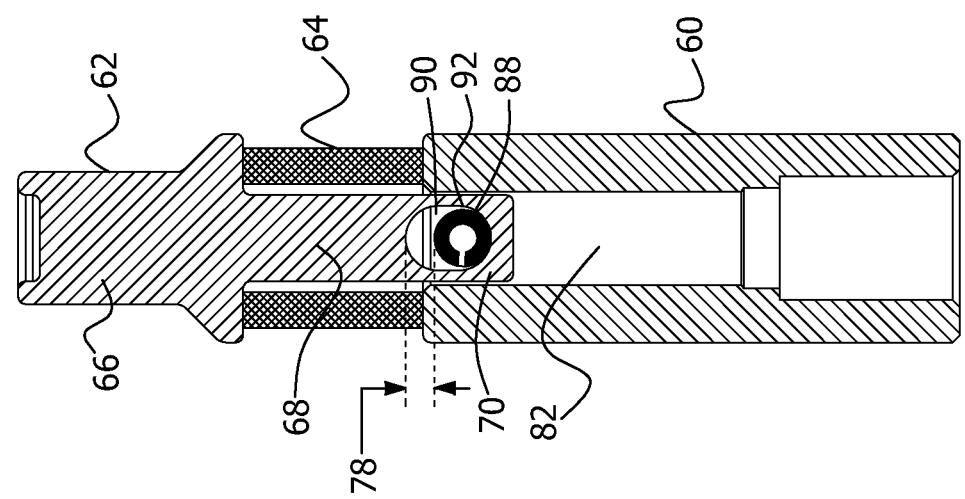

Referring to FIGS. 8A, 8B and 8C, there is shown another embodiment of the invention where a retention pin 88 connects the upper member 62 to the base member 60. In this embodiment, the anchor portion is preferably an extension of the neck portion with a same cross-section, and is provided with a pin hole 90 extending therethrough for receiving the retention pin 88. Similarly, the base member has a pin channel 92 extending transversally therethrough, in alignment with the pin hole 90 of the upper member. The pin channel 92 and pin hole 90 are sized to provide a longitudinal clearance 78 for the pin 88 therein, thereby defining the longitudinal play between the upper member 62 and base member 60.

FIG. 9 shows yet another embodiment of the invention, wherein the base member 60 is provided with comprises a recess 96 extending longitudinally therein and opening upwardly. The resilient middle element 64 is received at least partially within this recess 96, the bottom surface of which defining in this case the abutment surface 74.

The resilient middle element may be embodied by various resilient components, which are preferably selected in view of the particular application to which the valve is destined. With reference to FIGS. 6B and 8A, there are shown examples of plungers where the resilient middle element is embodied by a resilient sleeve or ring made of an appropriate polymer or silicone material. Such an embodiment would be particularly appropriate for applications where the required sealing force is light, as for low pressure operation. When the required sealing force is in the medium range, as for example for a few hundred pounds of process pressure into the valve, a helicoids shape spring could be use as show in FIGS. 7A and 8B. Alternatively, when the required sealing force must be higher, as for example for a thousand pound and higher, a Belleville type springs system could be use as show in FIGS. 7B and 8C. Alternatively, the resilient middle element can consist of a washer, made for example of Teflon™, or be composed of a plurality of components combined together, such as for example a stack of discs made of a compressible material. Advantageously, through a proper selection of the resilient component of the resilient middle element, it is therefore possible to tune the required sealing force for a particular application. The plungers of a given valve may be easily disassembled to change the middle element and therefore adapt the valve to different pressure requirements of a given application. Alternatively, the plungers themselves may be changed or an entirely different valve may be used for different applications.

Referring to FIGS. 10A, 10B, 11A, 11B, 12A, 12B and 13A to 13C, there are shown embodiments of the invention where a transversal play is provided between the upper member and base member, thereby providing for the upper member to be self-aligning within the corresponding passage.

With known plungers for typical diaphragm-sealed valves, slight variations coming from the manufacturing process or the assembly process may cause a plunger to be slightly slanted or misaligned relative to their respective plunger passage. Misalignments can also appear with time due to extensive use and may cause a plunger to rub or scratch the inner surface of its corresponding plunger passage, leading to a premature wear of the valve. The friction of the plunger against the inner surface of the passage may generate particles which, when accumulating on the top surface of the plunger, eventually prevent the proper closing of the ports by the plungers. More specifically, the plungers, generally made of stainless steel, when rubbing against the inner surface of the plunger passages, also made of stainless steel, generate particles accumulating on top of the plunger, causing variations of lengths amongst the set of plungers attached to a specific piston, which will eventually prevent the proper closing of the ports by the plungers and affect the overall functioning of the valve.

In some valves, plastic sleeves are placed around the plunger to facilitate their sliding into the plunger passages. In case of misalignment, the base of the plunger may also rub against the sleeved surface and generate plastic dust which may also eventually prevent the proper functioning of the valve, especially in cases where the valve has endured extensive cycling.

In the embodiment of FIGS. 10A and 10B, the bore 82 and cavity 76 of the base member 60 are sized to provide a transversal clearance 98 for the neck portion 68 and anchor portion 70 therein, thereby defining a transversal play between the upper member 62 and base member 60. This transversal play allows the upper member 62 of the plunger to move radially with respect to the base member 60. As will be understood by one skilled in the art, if the plunger 34 is misaligned or slanted relative to its corresponding plunger passage, the upper member 62 will be able to self-align in the passage since it can move both longitudinally and transversally with respect to the passage.

Similarly, in the embodiment of FIGS. 14, 14A, 14B and 15A to 15C, the pin channel 92 and pin hole 90 are also sized to provide a transversal clearance 98 for the pin 88 therein, thereby defining a transversal play between the upper member 62 and base member 60.

Both the longitudinal play and transversal play provided between the base member 60 and upper member 62 need only be over a range sufficient to allow a slight relative movement between these components. For example for a typical plunger the longitudinal clearance 78 may be as small as in the order of 0.005" (five-thousandths of an inch) while the transversal clearance 98 may vary between 0.002" and 0.0020". Of course, these measures are provided as examples only and other clearance dimensions may be used.

Of course, although the plungers shown in all the illustrated embodiments discussed above have lengths corresponding to the "longer" normally opened plungers, it will be understood that a similar structure may equally be applied to normally closed plungers.

Figure 16A:
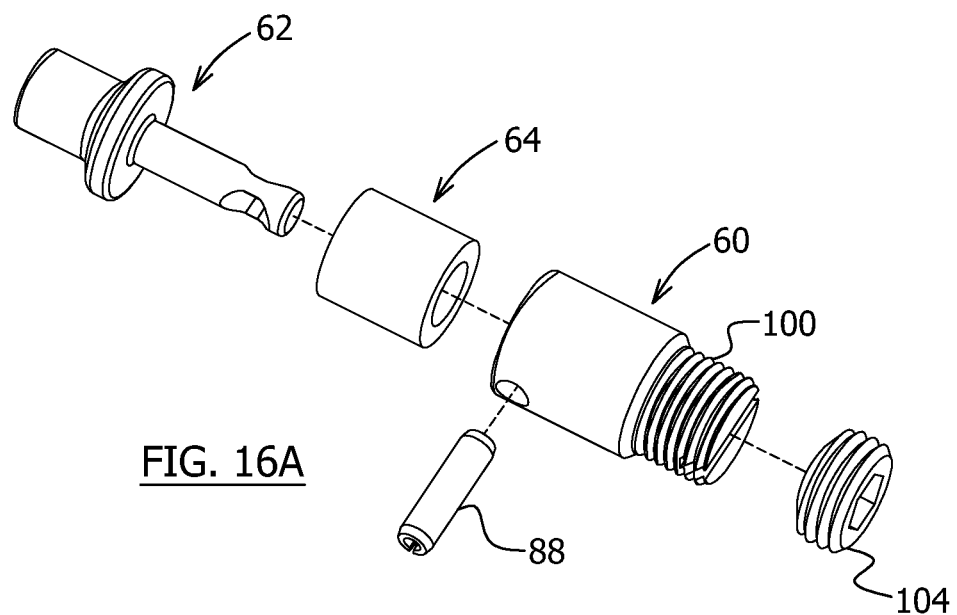
FIGS. 16A and 16B are perspective exploded views of plungers having an adjustable base section according to embodiments of the invention.
Figure 16B:
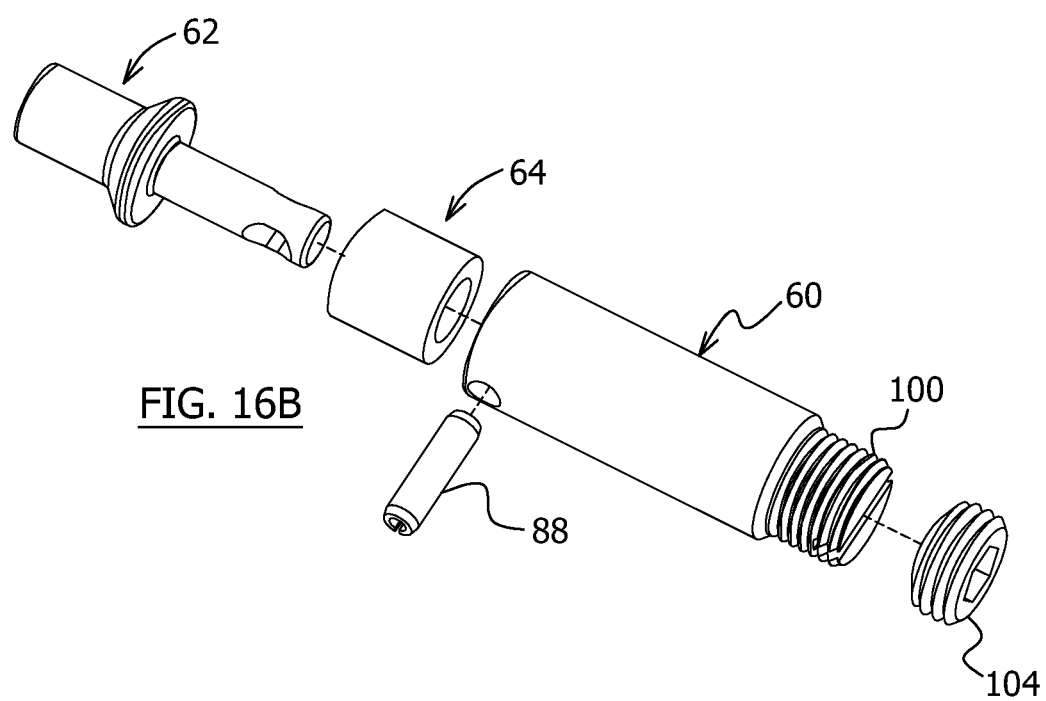
Figure 17:
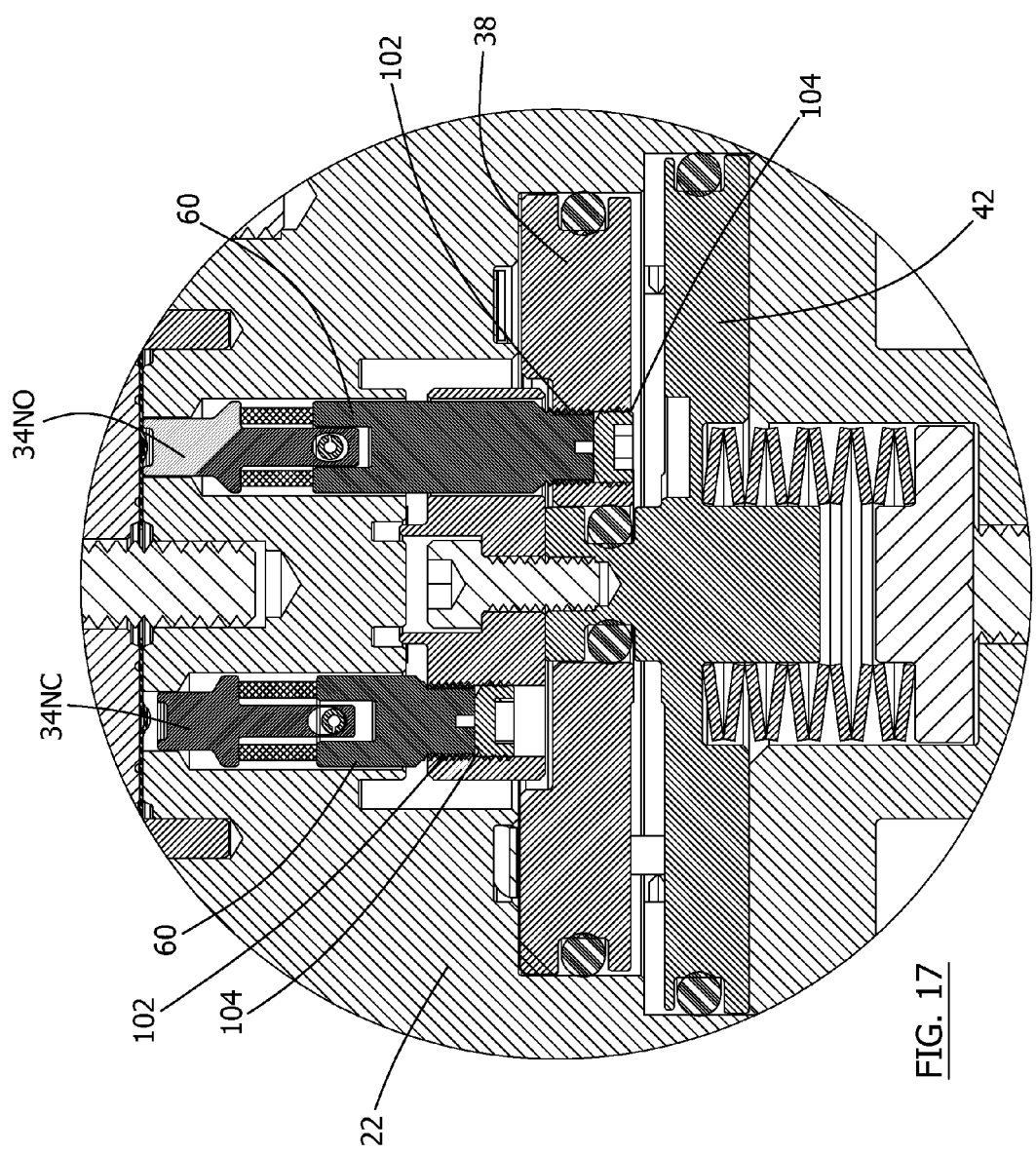
FIG. 17 is a cross sectional view of a portion of a plunger assembly incorporating plungers according to the embodiments of FIGS. 16A and 16B.

Referring to FIGS. 16A, 16B and 17 an alternative embodiment of the invention is shown where the base section of each plunger is attached to the corresponding part of the actuating mechanism of the valve through an adjustable attachment mechanism. In this embodiment, the base member 60 of the plunger has a threaded bottom portion 100, and each support element movable within said valve body with respect to said diaphragm-contacting surface, such as for example the push plate or the upper piston in the actuating mechanisms described herein, is provided with a corresponding threaded opening 102 for receiving the threaded bottom portion of each plunger.

The plunger shown in FIG. 16A has a shorter base section as would typically embody a NC plunger, whereas the plunger shown in FIG. 16B has a length typical of a NO plunger. Both variants are shown in a valve body in FIG. 17, where the NC plunger is affixed to the push plate and the NO plunger is affixed to the upper piston.

In the illustrated embodiment, the push plate and the upper piston are provided with the above-mentioned threaded openings 102 for collaborating with a threaded bottom portion 100 of the corresponding plungers. Rotating the plunger therefore allows fine-tuning the position of the base member of the plunger within the passage, and adjusts the effective length of the remainder of the plunger projecting from the push plate or upper piston. This embodiment advantageously makes it possible to adjust the sealing force of the plungers on the diaphragm within the working compression range of the middle portion of the plungers. A locking set screw 104 is provided within each threaded opening 102 underneath the corresponding plunger 34 and collaborates therewith to lock and avoid any rotation of the plunger 34 while the valve is in use. An appropriate sealing device, such as an O-ring 106 or the like, may be provided between the locking set screw 104 and the plunger 34 to avoid pneumatic actuation gas leaks through the piston. The use of a plunger construction where the head portion is rotationally free with respect to the base member, such as for example shown in FIGS. 6B, 7A, 7B and 9, in combination with this embodiment would offer the advantage of avoiding any twisting of the plunger when adjusting the base member within the threaded opening 102. While the embodiments of the plungers 34 illustrated are similar to that shown in FIG. 11a, it will be appreciated that other embodiments of the plungers 34, including but not limited to those having transversal play, could similarly be used.

Figure 18:
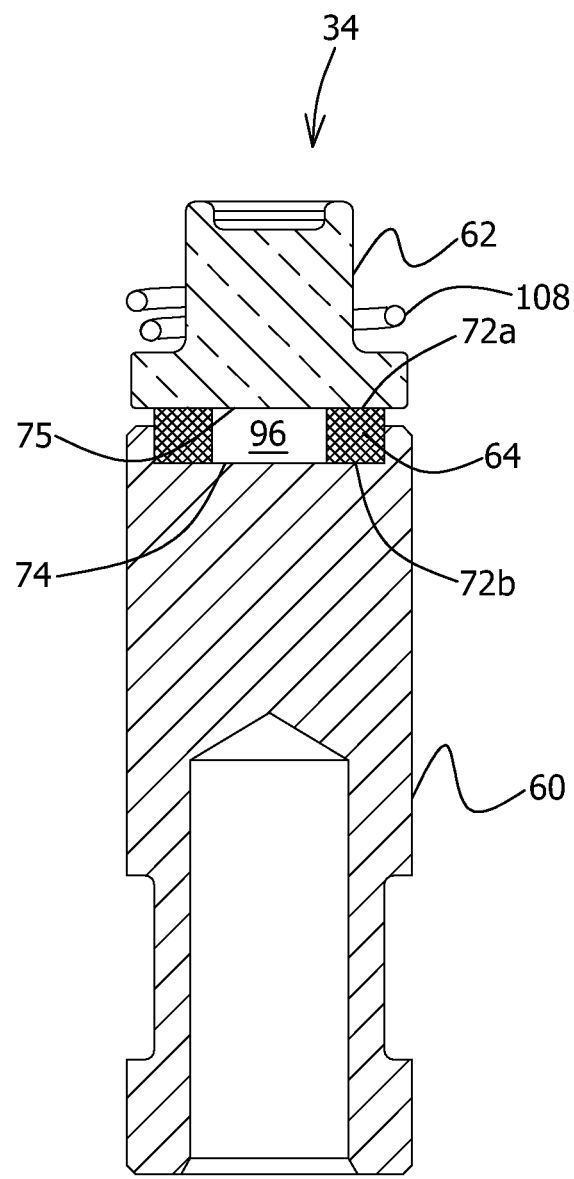
FIG. 18 is a cross-sectional view of a plunger according to yet another embodiment of the invention, where the upper member is not interlocked with the base member.

Referring to FIG. 18, there is shown a plunger 34 according to yet another embodiment of the invention, where the upper member 62 is generally "hat" shaped and is not directly interlocked with the base member 60. In this case, the base member 60 and upper member 62 have opposite abutment surfaces 74 and 75 facing each other, and in abutment with the opposite ends 72b and 72a of the resilient middle element 64. Preferably, the base member 60 includes a recess 96 in which the resilient middle element 64 is at least partially received the bottom surface of the recess 96 defining the abutment surface 74 of the base member 60.

Figure 19:
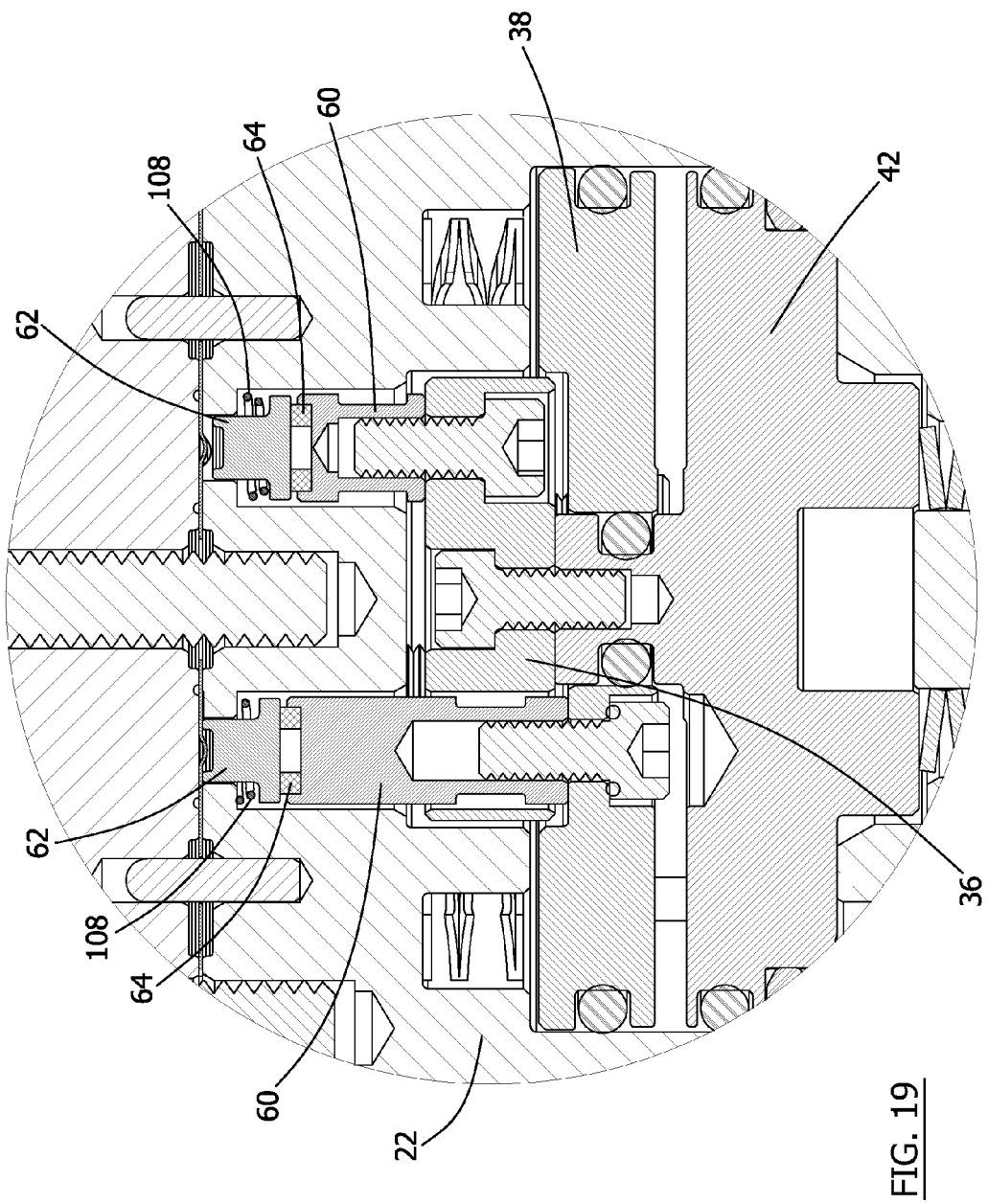
FIG. 19 is a cross sectional view of a portion of a plunger assembly incorporating plungers according to the embodiment of FIG. 18.

In this embodiment, the plunger 34 is preferably used in combination with a spring element 108 insertable in the passage with the plunger 34 to bias the upper member 62 away from the diaphragm-contacting surface. FIG. 19 shows a portion of a plunger assembly incorporating plungers 34 and spring elements 108 according to this embodiment. The spring element 108 may be embodied by any biasing means apt to bias the upper member 62 away from the diaphragm when the plunger 34 is retracted towards the opened position.

It will be noticed that the strokes of both the upper and lower pistons are limited by a shoulder in the valve body. As a result, an increase in actuating pressure will not move the pistons further than their predetermined stroke and will not change the force applied to the plungers. Preferably, the stroke of each piston is such as they will compress the middle section of the respective plungers to the "tune value" without having the plunger base section forcing against the upper plunger section.

Advantageously, plungers according to embodiments of the invention may mitigate or eliminate altogether the tight requirements for plunger lengths in prior art valves. It may also allow for a greater tolerance for variations in diaphragm thickness.

Preferably, the biasing force applied by the middle compressible section force varies as a function of the ambient temperature, thereby constituting an active temperature mechanical feedback loop built-in into the valve mechanism. This could be for example achieved by selecting a material for the resilient middle element having an appropriate material temperature characteristic. In this manner, the force acting against the diaphragm when the plunger is in the closed position could be decreases as the operating temperature increases, eliminating the risk of overstressing the diaphragm.

Figure 20:
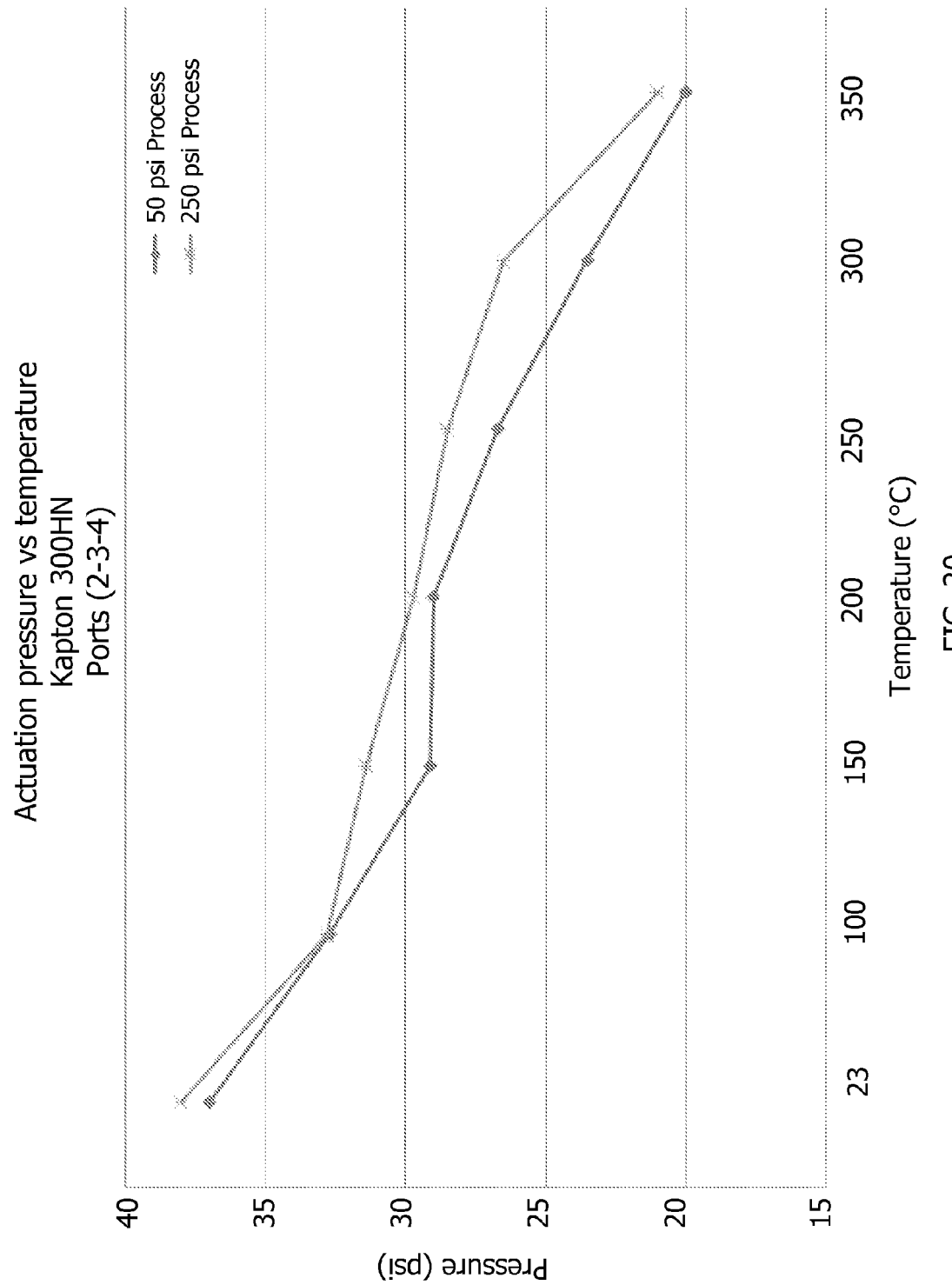
FIG. 20 is a graphic of the actuating pressure required to maintain proper sealing of a typical polymer diaphragm-sealed valve.

FIG. 20 shows an example of the measured decrease in pneumatic actuating pressure required to maintain proper sealing between ports of a typical diaphragm-sealed valve when the operating temperature is increased. As can be seen, less force is required due to the fact that the polymer base diaphragm is softer at higher temperature. Under this operating condition, it is easy to deform it, and furthermore the diaphragm show better sealing properties at higher temperature. This is because its surfaces is less ductile and fills more the surface finish of the valve head.

As mentioned above, at higher temperature the diaphragm is softer, and therefore more fragile. Maintaining the same actuating pressure than the one used at ambient temperature will have a detrimental effect on the overall performance of the valve, which could also be permanently damage. Preferably temperature characteristics of the plunger's resilient middle element are therefore selected in accordance with the temperature characteristics of the diaphragm. As different types of diaphragm material and thickness can be use, different compensation material characteristic could also be use.

The above example is not limitative. Those skilled in the art will understand that the resilient middle element of the plungers define a thermal feedback loop. Base on material selection and the combination used to make the compressible section, the system could be made to decrease, increase or maintain constant the force applied on the diaphragm when the temperatures rise.

In addition, it will be appreciated that for those embodiments comprising a transversal play between the upper member and its corresponding passage, misalignments of the plunger relative to its corresponding passage may be compensated for by allowing the upper member of the plunger to align itself with the passage. Advantageously, this self-alignment can improve the overall valve performance by reducing the friction of the plunger against the inner surface of the passage, which in turn can reduce plunger wear and the subsequent generation and accumulation of particles within the system.

One could also imagine that the pistons could be move by other means than pneumatic. Electrical mean such as solenoid or motor could also be considered. In the pneumatic actuation describe herein, the Belleville springs mounted in the bottom of the valve body are not used to set the normally close plungers force as with prior art valve, but to set the pressure value at which the normally close ports will open, since the sealing force is fix by the compressible middle section of the plungers. This characteristic make a big difference compare to prior art. Indeed, depend on N.C. Piston Belleville washer compressibility factor, the valve actuation pressure could be adjusted, and the time that all plungers are up (to avoid various flowpath mixing upon actuation) is also adjustable. This is another benefit of the pneumatic base actuator of the embodiments described above.

Of course, numerous modifications could be made to the embodiments described above without departing from the scope of the present invention.

What is claimed is:

1. A diaphragm-sealed valve comprising:
   a valve cap having a cap interface;
   a valve body having a body interface and several cylindrical passages extending in the valve body and opening on said body interface;
   a diaphragm compressed between the valve cap and the valve body interfaces;
   several normally-closed and normally-open plungers slidably provided in the respective passages of the valve body,
   a plunger-actuating assembly comprising:
      disk-shape upper and lower pistons located within a circular cavity of the valve body, the lower piston extending under the upper piston contiguously thereto, said pistons being free to rotate relative to the valve body over a given radial distance;
      an actuator for controlling a distance between the upper and lower pistons for actuating the plungers between closed and open positions,
   each of said plungers comprising:
      a base member operatively linked to one of the lower and upper pistons;
      an upper member projecting towards said diaphragm; and
      a resilient middle element provided between the base member and the upper member;
      said base and upper members being sized, shaped and configured for providing a transversal play between said base and upper members, the transversal play corresponding to the radial distance over which the pistons can rotate, the base member movable between a first position where the base member is coaxial with the upper member and a second position where the base member is not coaxial with the upper member upon rotation of one of the lower and upper pistons within the circular cavity, for preventing slanting of the plungers within their respective passages.

2. The diaphragm-sealed valve according to claim 1, wherein for each of the plungers, the base member comprises a circular recess extending therearound and opening upwardly, the resilient middle element being at least partially received within said recess, a bottom surface of said recess defining the abutment surface.

3. The diaphragm-sealed valve according to claim 1, wherein for each of the plungers, the base member of each of said plungers has a threaded bottom portion, and said plunger-actuating assembly comprises at least one support element movable within said valve body with respect to said diaphragm-contacting surface, the at least one support element being provided with a corresponding threaded opening, the threaded bottom portion of each plunger being screwed within said threaded opening of the support element, thereby avoiding use of a screw for retaining the plunger to the support element.

4. The diaphragm-sealed valve according to claim 3, wherein the at least one support element comprises:
   a push plate extending within the valve body in parallel to the diaphragm-contacting surface and movable transversally thereto, the normally closed plungers being mounted on said push plate, a plurality of cavities extending across said push plate for allowing the normally open plungers therethrough, the lower piston being rigidly connected to the push plate; and
   the upper piston extending under the push plate contiguously thereto, the normally opened plungers being placed thereon.

5. The diaphragm-sealed valve according to claim 4, wherein the plunger actuating mechanism further comprises:
   biasing means for upwardly biasing the lower piston and downwardly biasing the upper piston; and
   actuating means for actuating the plungers between opened and closed positions thereof, the actuating mechanism controlling the distance between the upper and lower pistons.

6. The diaphragm-sealed valve according to claim 1, wherein:
   each of said several passages has an upper section opening on said body interface and a lower section, the upper and lower sections having with respective diameters, the diameter of the upper section being smaller than the diameter of the lower section;
   for each of the plungers:
      the upper member comprises a head portion having a cylindrical end, for compressing said diaphragm when in a closed position, a neck portion holding the resilient middle element and an anchor portion interlocked with the base member, said cylindrical end being slidably fitted the upper section of a corresponding one of said several passages;
      the base member has an abutment surface; and
      the resilient middle element has opposite ends in abutment with the head portion of the upper member and the abutment surface of the base member, respectively.

7. The diaphragm-sealed valve according to claim 6, wherein for each of the plungers, the abutment surface of the base member extends on top of the base member.

8. The diaphragm-sealed valve according to claim 6, wherein for each of the plungers, the upper member is rotationally free with respect to the base member.

9. The diaphragm-sealed valve to claim 6, wherein for each of the plungers:
   the anchor portion of the upper member has a width greater than said neck portion; and
   the base member comprises a cavity for receiving said anchor portion,
   said cavity being sized to provide a transversal clearance for the anchor portion therein to define said transversal play.

10. The diaphragm-sealed valve according to claim 9, wherein for each of the plungers, the base member further comprises a bore extending longitudinally therein and having opposite extremities opening on the abutment surface of said base member and said cavity, respectively, the bore being sized to receive a section of the neck portion of the upper member therein, a transition between the bore and cavity defining a shoulder for holding the anchor portion within said cavity.

11. The diaphragm-sealed valve according to claim 10, wherein for each of the plungers, the cavity is sized to provide a longitudinal clearance for the anchor portion therein, thereby defining a longitudinal play between the upper member and base member.

12. The diaphragm-sealed valve according to claim 6, wherein each of the plungers further comprises a retention pin for connecting the upper member to the base member, the retaining pin fitting completely within said base member, so as to avoid contacting the sidewall of the corresponding passage of the valve body.

13. The diaphragm-sealed valve according to claim 12, wherein for each of the plungers, the base member and anchor portion of the upper member, respectively, have a pin channel and a pin hole transversally extending therethrough, the retaining pin being inserted in said pin channel and pin hole.

14. The diaphragm-sealed valve according to claim 13, wherein for each of the plungers, wherein said pin channel and pin hole are sized to provide a transversal clearance for the pin therein, thereby defining the transversal play between the upper member and base member.

15. A diaphragm-sealed valve comprising:
   a valve cap having a cap interface;
   a valve body having a body interface and several cylindrical passages extending in the valve body, said passages having an upper section opening on said body interface and a lower section, the upper and lower sections having with respective diameters, the diameter of the upper section being smaller than the diameter of the lower section;
   a diaphragm compressed between the valve cap and the valve body interfaces;
   several normally-closed and normally-open plungers slidably provided in the respective passages of the valve body,
   a plunger-actuating assembly comprising:
      disk-shape upper and lower pistons located within a circular cavity of the valve body, the lower piston extending under the upper piston contiguously thereto, said pistons being free to rotate relative to the valve body over a given radial distance;
      an actuator for controlling a distance between the upper and lower pistons for actuating the plungers between closed and open positions,
   each of said plungers comprising:
      a base member operatively linked to one of the lower and upper pistons, the base member having a cross section diameter smaller than the diameter of the lower section of the passages;
      an upper member having a head portion projecting towards said diaphragm, said head portion closely fitting within the upper section of the corresponding channel
      a resilient middle element provided between the base member and the upper member;
   wherein the base member is movable transversally relative to the upper member over a distance corresponding to the given radial distance over which the upper and lower pistons can rotate, whereby rotation of one of the lower and upper pistons within the circular cavity forces a radial displacement of the base member relative to the upper member, while the upper member remains aligned within the upper section of the passage.

* * * * *

UNITED STATES PATENT AND TRADEMARK OFFICE
CERTIFICATE OF CORRECTION

| | | |
|---|---|---|
| PATENT NO. | : 8,851,452 B2 | Page 1 of 5 |
| APPLICATION NO. | : 13/256381 | |
| DATED | : October 7, 2014 | |
| INVENTOR(S) | : Gamache et al. | |

It is certified that error appears in the above-identified patent and that said Letters Patent is hereby corrected as shown below:

In the Specification

\*Col. 1, line 37;
  "slideably" should be --slidably--;

\*Col. 1, line 41;
  "valve" should be --valves--;

\*Col. 1, line 51;
  "cycles" should be --cycled--;

\*Col. 1, line 52;
  "operate" should be --operated--;

\*Col. 1, line 53;
  "temperature" should be --temperatures--;

\*Col. 1, line 67;
  "dimensions" should be --dimension--;

\*Col. 2, line 15;
  "normally closed" should be --"normally closed"--;

\*Col. 2, line 37;
  "use" should be --used--;

\*Col. 2, line 50;
  "over the time" should be --over time--;

\*Col. 3, line 58;
  "cross sectional" should be --cross-sectional--;

\*Col. 3, line 62;
  "cross sectional" should be --cross-sectional--;

Signed and Sealed this
Twenty-eighth Day of April, 2015

Michelle K. Lee
*Director of the United States Patent and Trademark Office*

*Col. 4, line 6;
   "FIG." should be --FIGS.--;

*Col. 4, line 6;
   "cross-section" should be --cross-sectional--;

*Col. 4, line 42;
   "cross sectional" should be --cross-sectional--;

*Col. 4, line 48;
   "cross sectional" should be --cross-sectional--;

*Col. 4, line 60;
   "of type" should be --of a type--;

*Col. 5, line 3;
   "open" should be --opens--;

*Col. 5, line 6;
   "plungers" should be --plunger--;

*Col. 5, line 15;
   "slideable" should be --slidable--;

*Col. 5, lines 39-40;
   "transversally" should be --transversely--;

*Col. 5, line 65;
   "extend" should be --extends--;

*Col. 6, line 16;
   "pressurised" should be --pressurized--;

*Col. 6, line 58;
   "force" should be --forced--;

*Col. 6, line 67;
   "respectively abuts" should be --respectively and abuts--;

*Col. 7, line 6;
   "disk" should be --disc--;

*Col. 7, line 34;
   "transversally" should be --transversely--;

*Col. 7, line 40;
   "with comprises a" should be --with a--;

*Col. 7, line 56;
   "use as show" should be --used as shown--;

*Col. 7, line 58;

"pound" should be --pounds--;

*Col. 7, line 59;

"springs" should be --spring--;

*Col. 7, line 59;

"use as show" should be --used as shown--;

*Col. 8, line 14;

"their" should be --its--;

*Col. 8, lines 47-48;

"transversally" should be --transversely--;

*Col. 9, line 43;

"11a" should be --11A--;

*Col. 9, line 54;

"partially received the" should be --partially received in the--;

*Col. 10, line 21;

"decreases" should be --decreased--;

*Col. 10, line 29;

"temperature" should be --temperatures--;

*Col. 10, lines 31 and 32;

"show...temperature" should be --shows...temperatures--;

*Col. 10, line 32;

"surfaces" should be --surface--;

*Col. 10, line 32;

"more the" should be --more of the--;

*Col. 10, line 34;

"temperature" should be --temperatures--;

*Col. 10, line 38;

"damage" should be --damaged--;

*Col. 10, line 42;

"use" should be --used--;

*Col. 10, line 43;

"characteristic...use" should be --characteristics...used--;

*Col. 10, line 46;

"define" should be --defines--;

*Col. 10, line 46;

"Base" should be --Based--;

*Col. 10, line 62;

"move" should be --moved--;

*Col. 10, line 63;

"mean" should be --means--;

*Col. 10, lines 66 and 67;

"close plungers" should be --closed plunger's--;

*Col. 11, line 1;

"close" should be --closed--;

*Col. 11, line 2;

"fix" should be --fixed--;

*Col. 11, line 3;

"make...compare" should be --makes...compared--;

*Col. 11, line 4;

"depend on N.C. Piston" should be --depending on the NC piston--;

*Col. 11, line 8;

"base" should be --based--;

In the Claims

*Col. 11, claim 1, line 23;

"body" should be --body;--;

*Col. 11, claim 1, line 25;

"disk-shape" should be --disc-shaped--;

*Col. 11, claim 1, line 32;

"positions," should be --positions;--;

*Col. 11, claim 1, line 37;

"said diaphragm; and" should be --said diaphragm;--;

*Col. 11, claim 1, line 39;

"member;" should be --member; and--;

*Col. 12, claim 4, lines 4-5;

"transversally" should be --transversely--;

*Col. 12, claim 6, line 26;

"having with respective" should be --having respective--;

*Col. 12, claim 6, line 35;

"fitted the" should be --fitted to the--;

*Col. 12, claim 9, line 48;

"valve to" should be --valve according to--;

*Col. 12, claim 9, line 51;

"neck portion; and" should be --neck portion;--;

*Col. 12, claim 9, line 53;

"portion" should be --portion; and--;

*Col. 13, claim 12, line 7;

"retaining" should be --retention--;

*Col. 13, claim 13, line 14;

"transversally" should be --transversely--;

*Col. 13, claim 13, line 14;

"retaining" should be --retention--;

*Col. 13, claim 15, line 27;

"having with respective" should be --having respective--;

*Col. 14, claim 15, line 3;

"body," should be --body;--;

*Col. 14, claim 15, line 5;

"disk-shape" should be --disc-shaped--;

*Col. 14, claim 15, line 12;

"positions," should be --positions;--;

*Col. 14, claim 15, line 14;

"cross section" should be --cross-sectional--;

*Col. 14, claim 15, line 20;

"channel" should be --channel;--; and

*Col. 14, claim 15, line 23;

"transversally" should be --transversely--.